(12) United States Patent
Dufour et al.

(10) Patent No.: US 11,273,210 B2
(45) Date of Patent: Mar. 15, 2022

(54) ARGININE DEIMINASE ENCAPSULATED INSIDE ERYTHROCYTES AND THEIR USE IN TREATING CANCER AND ARGINASE-1 DEFICIENCY

(71) Applicant: ERYTECH PHARMA, Lyons (FR)

(72) Inventors: Emmanuelle Dufour, Lyons (FR); Manuel Blanc, Lyons (FR); Aurélien Meyzaud, Lyons (FR)

(73) Assignee: ERYTECH PHARMA, Lyons (FR)

( * ) Notice: Subject to any disclaimer, the term of this patent is extended or adjusted under 35 U.S.C. 154(b) by 0 days.

(21) Appl. No.: 16/643,431

(22) PCT Filed: Jun. 29, 2018

(86) PCT No.: PCT/EP2018/067679
§ 371 (c)(1),
(2) Date: Feb. 28, 2020

(87) PCT Pub. No.: WO2019/042628
PCT Pub. Date: Mar. 7, 2019

(65) Prior Publication Data
US 2020/0254074 A1    Aug. 13, 2020

(30) Foreign Application Priority Data
Aug. 31, 2017 (EP) ..................................... 17306122
Dec. 28, 2017 (JP) ............................. JP2017-254383

(51) Int. Cl.
| A61K 38/50 | (2006.01) |
| A61P 43/00 | (2006.01) |
| A61K 35/18 | (2015.01) |
| C12N 5/078 | (2010.01) |

(52) U.S. Cl.
CPC .............. *A61K 38/50* (2013.01); *A61K 35/18* (2013.01); *A61P 43/00* (2018.01); *C12N 5/0641* (2013.01)

(58) Field of Classification Search
None
See application file for complete search history.

(56) References Cited

U.S. PATENT DOCUMENTS

| 7,413,735 | B2 * | 8/2008 | Min | ............... | C12Y 305/03006 |
| | | | | | 424/94.5 |
| 9,125,876 | B2 | 9/2015 | Godfrin et al. | | |
| 9,968,663 | B2 | 5/2018 | Godfrin et al. | | |
| 10,286,008 | B2 * | 5/2019 | Godfrin | ............... | A61K 9/5068 |
| 2008/0274092 | A1 | 11/2008 | Godfrin et al. | | |
| 2016/0030532 | A1 * | 2/2016 | Godfrin | ................... | A61P 7/00 |
| | | | | | 424/93.73 |
| 2019/0167770 | A1 * | 6/2019 | Rowlinson | ................ | A61P 3/00 |

FOREIGN PATENT DOCUMENTS

EP    2295560 A1 *    3/2011

OTHER PUBLICATIONS

Takaku H. et al. In vivo Anti-Tumor Activity of Argnine Deiminase Purified from Mycoplasma arginini. Int J of Cancer 51(2)244-249, 1992. (Year: 1992).*
European Search Report for EP 17306122, dated Feb. 1, 2018.
International Search Report for PCT/EP2018/067679, dated Aug. 16, 2018.
Written Opinion of the International Searching Authority for PCT/EP2018/067679, dated Aug. 16, 2018.
Fabien Gay et al: "Abstract 4812: Arginine deiminase loaded in erythrocytes: a promising formulation for L-arginine deprivation therapy in cancers : Cancer Research", Cancer research, Jul. 15, 2016 (Jul. 15, 2016), XP055446397, Retrieved from the Internet: URL:http://cancerres.aacrjournals.org/content/76/14 Supplement/4812 [retrieved on Jan. 31, 2018] abstract.
Park I-Set al: "Arginine deiminase: A potential inhibitor of angiogenesis and tumour growth", British Journal of Cancer, Nature Publishing Group, GB, vol. 89, No. 5, Sep. 1, 2003 (Sep. 1, 2003), pp. 907-914, XP002369974, ISSN: 0007-0920, DOI: 10.1038/SJ.BJC.6601181 p. 907, left-hand column, paragraph 1-right-hand column, paragraph 1.
Laurel L. Ballantyne et al: "Liver-specific knockout of arginase-1 leads to a profound phenotype similar to inducible whole body arginase-1 deficiency", Molecular Genetics and Metabolism Reports, vol. 9, Dec. 1, 2016 (Dec. 1, 2016), pp. 54-60, XP055446496, ISSN: 2214-4269, DOI: 10.1016/j.ymgmr.2016.10.003 pp. 58-59.
Sin Yuan Yan et al: "Arginase-1 deficiency", Journal of Molecular Medicine, Springer Verlag, DE, vol. 93, No. 12, Oct. 14, 2015 (Oct. 14, 2015), pp. 1287-1296, XP035801319, ISSN: 0946-2716, DOI: 10.1007/800109-015-1354-3 [retrieved on Oct. 14, 2015] p. 1292, left-hand column, last paragraph-p. 1293, left-hand column, paragraph 1.

(Continued)

*Primary Examiner* — Ralph J Gitomer
(74) *Attorney, Agent, or Firm* — B. Aaron Schulman, Esq.; Stites & Harbison, PLLC

(57) ABSTRACT

The present invention is related to arginine deiminase encapsulated into erythrocytes for use in therapy. It is in particular related to the use thereof in treating arginase-1 deficiency. Also, it relates to novel pharmaceutical compositions comprising arginine deiminase from *M. arginini* encapsulated into erythrocytes and the use thereof in treating diseases that may benefit from arginine depletion, such as arginine dependent cancers, in particular arginine-auxotrophic cancers, and arginase-1 deficiency.

Figure 1:
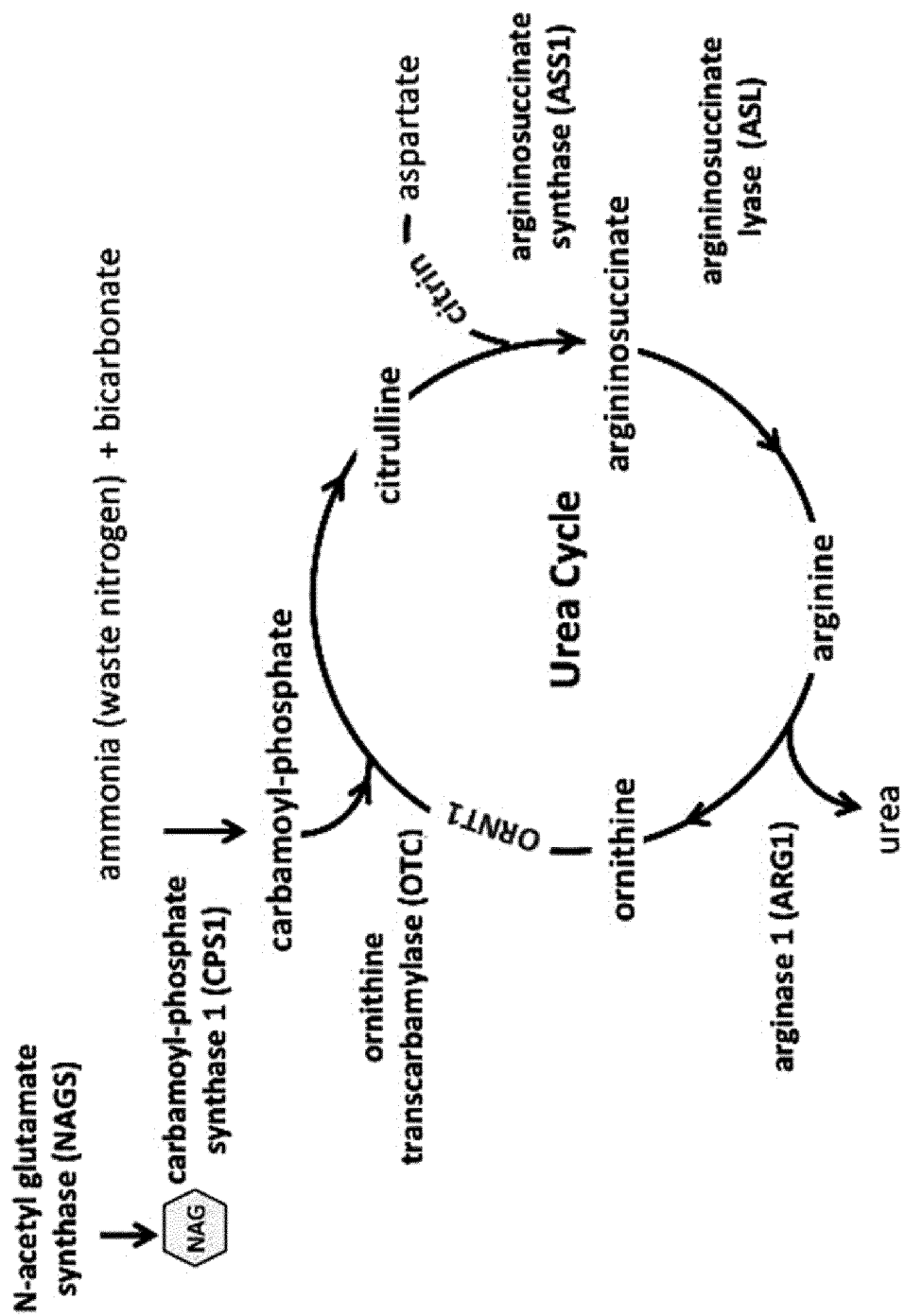

19 Claims, 7 Drawing Sheets
Specification includes a Sequence Listing.

(56) References Cited

OTHER PUBLICATIONS

Lyon, France, "Erytech Announces Collaboration with Queen's University to Advance its Product Candidate for Rare Metabolic Disorders", Jul. 12, 2017 (Jul. 12, 2017), ERYP Listed Euronext erytech@newcap.eu.

Lyon, France, "News Release—Erytech collaborates with Queen's University to advance its platform in the field of rare metabolic disorders", Friday, Jun. 30, 2017 (Jun. 30, 2017), Queens's Gazette Media Centre http://www.queensu.ca/gazette/media/news-release-erytech-collaborates-queens-university.

\* cited by examiner

ARGININE DEIMINASE ENCAPSULATED INSIDE ERYTHROCYTES AND THEIR USE IN TREATING CANCER AND ARGINASE-1 DEFICIENCY

The present patent application claims priority to the earlier filed European patent application No. 17306122.7 filed Aug. 31, 2017 and Japanese patent application No. 2017-254383 filed Dec. 28, 2017.

The present invention is related to arginine deiminase encapsulated into erythrocytes for use in therapy. It is in particular related to the use thereof in treating arginase-1 deficiency. Also, it relates to novel pharmaceutical compositions comprising arginine deiminase from *M. arginini* encapsulated into erythrocytes and the use thereof in treating diseases that may beneficiate from arginine depletion, such as arginine dependent cancers, in particular arginine-auxotrophic cancers, and arginase-1 deficiency.

BACKGROUND OF THE INVENTION

Arginine is a semi-essential amino acid. It is synthesized in the course of the urea cycle from citrulline in two stages owing to the action of arginosuccinate synthetase and arginosuccinate lyase. Arginine is metabolized to ornithine under the action of arginase, and ornithine can in its turn be transformed into citrulline by a reaction catalyzed by ornithine transcarbamylase.

It has been shown that certain types of tumor cells require arginine to be supplied, and this led to consideration of arginine depletion being a possible treatment for these forms of cancers, called arginine-auxotrophic cancers. Arginine deiminase, an arginine-degrading enzyme, catalyzes the hydrolyzation of arginine to citrulline and ammonium by deamination of guanidine group. The antitumor activity of arginine deiminase has been the subject of numerous publications. Thus, in vivo activity of arginine deiminase has been demonstrated with respect to malignant melanoma and hepatocarcinoma. However, the enzyme arginine deiminase has some major drawbacks.

Arginine deiminase is not produced in mammals but is obtained from microorganisms, making it a highly antigenic compound for mammals.

Moreover, this enzyme has a very short half-life in mammals, of the order of about 5 hours, and must be administered daily at a high dose to become effective.

To overcome these drawbacks for the treatment of cancer European patent EP1874341 proposes an original approach which consists in encapsulating arginine deiminase inside erythrocytes. EP1874341 notably discloses in example 3 page 10 the entrapment of arginine deiminase originated from *Pseudomonas aeruginosa*.

Arginase-1 deficiency is a rare genetic disorder affecting the final step of the urea cycle in the liver that converts waste nitrogen in the form of ammonia into urea for excretion in the urine. It is caused by mutations in the ARG1 gene resulting in partial or complete loss of arginase 1 enzyme which catalyzes the hydrolysis of arginine to ornithine and urea (see FIG. 1).

Arginase-1 deficient patients exhibit hyperargininemia, progressive neurological and intellectual impairment, persistent growth retardation and infrequent episodes of hyperammonemia.

There are currently no cures for arginase-1 deficiency and treatment outcomes are usually poor with a low-protein diet and/or nitrogen scavenger drugs. The main biochemical feature is accumulation of arginine leading to toxic levels of guanidino compounds and nitric oxide (Sin et al, PLoS ONE 8(11)). Because arginine and its metabolites are suspected to cause the neurologic phenotype in arginase-1 deficiency, the consensus goal of treatment has been reduction of plasma arginine with a low-protein diet, amino acid supplementation and administration of nitrogen-scavenging agents. However, with this treatment strategy, normalization or near-normalization of plasma arginine in arginase-1 deficiency is challenging.

Normalization of plasma arginine levels in arginase-1 deficiency is therefore challenging and the use of arginase enzyme therapy has been previously investigated. Burrage et al., for instance, have investigated a modified PEGylated human recombinant arginase enzyme in arginase-deficient mouse models (Burrage et al. Human Molecular Genetics, 2015, 24(22)). Although this enzyme led to a reduction of plasma arginine level it did not improve the survival of arginase-deficient mice likely because of persistence of hyperammonemia. Hyperammonemia is the main treatment challenge in arginase deficiency (Burrage et al. Human Molecular Genetics 24(22)).

Therefore, the discovery of alternative ways for the depletion of plasma arginine level in arginase deficiency has been a major goal for many years.

The reaction catalyzed by arginine deiminase is:

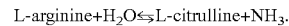

$$\text{L-arginine} + H_2O \leftrightarrows \text{L-citrulline} + NH_3.$$

It is an equilibrated reaction and scientific arguments exist in the scientific community suggesting that using arginine deiminase to treat arginase-1 deficiency would not be possible, because:

- This enzyme is of bacterial origin and may induce allergic reactions
- The products of the reaction catalyzed by arginine deiminase are citrulline and ammoniac:
- Citrulline can be converted back to arginine (see urea cycle in FIG. 1), and
- Ammoniac can be problematic in the context of arginase-1 deficiency where patients have episodes of hyperammonemia.

Contrary to those technical prejudices, the Applicant of the present invention unexpectedly found and demonstrated that arginine deiminase encapsulated into erythrocytes may be a novel treatment approach to reduce the toxic accumulation of arginine and its metabolic side products. The Applicant found, in particular, that the depletion of serum arginine levels achieved in mice by administering the composition of the present invention is high and therefore of therapeutic interest. The inventor demonstrated furthermore that said depletion of serum Arginine levels in Arginine-1 deficient mice is not accompanied by notable changes in ammonia levels. These results are especially surprising because of the existing technical prejudice according to which an arginine deiminase would not enable the treatment of arginase-1 deficiency because of the NH$_3$ production and a possible citrulline back-conversion.

Among the different arginine deiminase that can be encapsulated in erythrocytes, the applicant has identified a specific arginine deiminase that has characteristics that lead to an unexpected improvement of PK/PD parameters.

In particular, arginine deiminase obtained from the bacteria *Mycoplasma arginini* improves the PK/PD parameters. Moreover, said arginine deiminase from *Mycoplasma arginini* does not require any co-factor which is a desirable characteristic for its activity inside the erythrocyte. The arginine deiminase from *Mycoplasma arginini* therefore has technical advantages over known arginine deiminase and is therefore very suited for the use in context of the present invention. In addition, the arginine deiminase from *Mycoplasma arginini* is a homodimer with a molecular weight of 92 kDa and thus favorable for entrapment inside erythrocytes.

Using said arginine deiminase will thus be a great advance in Arginine depletion therapies such as cancer therapy, in particular arginine-auxotrophic cancers, and arginase-1 deficiency therapy.

SUMMARY OF THE INVENTION

An object of the invention is thus a pharmaceutical composition comprising arginine deiminase encapsulated into erythrocytes, for its use in treating arginase-1 deficiency.

The invention refers, in particular, to a pharmaceutical composition comprising arginine deiminase encapsulated into erythrocytes and a pharmaceutically acceptable vehicle, for its use in treating arginase-1 deficiency.

In one preferred embodiment, the arginine deiminase encapsulated into erythrocytes is from *M. arginini*.

Another object of the invention is a suspension of erythrocytes encapsulating arginine deiminase from *M. arginini*. Said suspension is in particular a suspension of erythrocytes encapsulating arginine deiminase from *M. arginini* in a pharmaceutical acceptable vehicle.

A further object of the invention is a pharmaceutical composition comprising the suspension of the invention for its use in treating arginase-1 deficiency or arginine-dependent cancers, treating or preventing of septic shock, inhibiting angiogenesis and treating angiogenesis associated diseases, in particular for its use in treating arginase-1 deficiency or arginine-dependent cancers.

Another object of the invention is a method for treating arginase-1 deficiency, comprising administering to a patient in need thereof an effective amount of the pharmaceutical composition of the invention or administering to a patient in need thereof an effective amount of arginine deiminase encapsulated into erythrocytes.

Another object of the invention is a method for treating arginase-1 deficiency or arginine-dependent cancers, treating or preventing of septic shock, inhibiting angiogenesis or treating angiogenesis associated diseases comprising administering to a patient in need thereof an effective amount of the pharmaceutical composition comprising arginine deiminase from *M. arginini* or an effective amount of arginine deiminase from *M. arginini* encapsulated into erythrocytes.

DETAILED DESCRIPTION

Arginine Deiminase

"Arginine deiminase" also referred to as "ADI" is an enzyme that catalyzes the chemical reaction: L-arginine+ $H_2O \leftrightarrows$ L-citrulline+$NH_3$. Accordingly, in context of the present invention the arginine deiminase used in context of the invention may also be referred to as "the enzyme" or ADI.

The two substrates of this enzyme are L-arginine and $H_2O$, whereas its two products are L-citrulline and $NH_3$. The arginine deiminase belongs to the family of hydrolases and is identified under reference EC 3.5.3.6 in IUBMB Enzyme Nomenclature. ADI may originate from different microorganisms, such as *Bacillus pyocyaneus, Pseudomonas putida, Halobacterium salinarium, Mycoplasma arginini, Mycoplasma hominis, Pseudomonas aeruginosa, Lactobacillus lactis* ssp. *Lactis*, and *Pseudomonas plecoglossicida* (see Rui-Zhi Han et aL, Appl. Microbiol. Biotechnol. 2016, 100: 4747-4760).

In one embodiment, the arginine deiminase is a protein. As used herein, the term "protein" includes single-chain polypeptide molecules as well as multiple-polypeptide complexes where individual constituent polypeptides are linked by covalent or non-covalent means.

As used herein, the terms "polypeptide" and "peptide" refer to a polymer in which the monomers are amino acids and are joined together through peptide or disulfide bonds. The terms subunit and domain may also refer to polypeptides and peptides having biological function.

The arginine deiminase employed in context of the present invention can be of natural, synthetic or artificial origin, or obtained by genetic engineering (for example production of the enzyme in a host cell, for example *E. coli*, after integration of a vector expressing the gene coding for the enzyme), and the person skilled in the art could refer, for example, to S. Misawa et al., J. of Biotechno. 36, 1994, 145-155 for the description of production of ADI from *M. arginini* in *E. coli*. Arginine deiminases that can be used are described, for instance, in EP-A-1 011 717, EP-A-0 414 007, U.S. Pat. No. 5,372,942, JP-A-6062867, JP-A-2053490, JP-A-2035081. In an equivalent manner, the invention includes the use of analogues of this enzyme, such as variants and fragments, which can notably be enzymes that have been modified in order to increase their enzymatic activity, as described for example in EP-A-0 981 607.

The present invention employs preferably improved ADI for use in any disease that benefits from the depletion of plasma arginine including, for example, arginine-dependent (auxotrophic) cancers and arginase deficiency.

Accordingly, in one preferred embodiment, the arginine deiminase used in context of the present invention is from *Mycoplasma arginini*. The arginine deiminase from *Mycoplasma arginini* is a homodimer with a molecular weight of 92 kDa. The relative small size of said arginine deiminase in comparison to other arginine deiminases is advantageous for the encapsulation in erythrocytes.

In one embodiment, the arginine deiminase from *Mycoplasma arginini* comprises the amino acid sequence of SEQ ID NO: 1 or variants or fragments thereof. The amino acid sequence of SEQ ID NO: 1 corresponds to the amino acid sequence of the arginine deiminase from *Mycoplasma arginini* as available from the GenBank database under NCBI reference number WP_004416214.1, as available on Aug. 22, 2017.

References herein to amino acid sequences (also referred to as polypeptides) include both, the particular amino acid sequences, and variants of said sequences.

"Variant proteins" may be naturally occurring variants, such as splice variants, alleles and isoforms, or they may be produced by recombinant means. Variations in amino acid sequence may be introduced by substitution, deletion or insertion of one or more codons into the nucleic acid sequence encoding the protein that results in a change in the amino acid sequence of the protein. Optionally the variation is by substitution of 1, 2, 3, 4, 5, 6, 7, 8, 9, 10, 11, 12, 13, 14, 15, 16, 17, 18, 19, 20 or more amino acids with any other amino acid in the protein. Additionally or alternatively, the variation may be by addition or deletion of 1, 2, 3, 4, 5, 6, 7, 8, 9, 10, 11, 12, 13, 14, 15, 16, 17, 18, 19, 20 or more amino acids within the protein.

"Fragments" of the proteins are also encompassed by the invention. Such fragments may be truncated at the N-terminus or C-terminus, or may lack internal residues, for example, when compared with a full length protein. Certain fragments lack amino acid residues that are not essential for enzymatic activity. Preferably, said fragments are at least about 10, 20, 30, 40, 50, 60, 70, 80, 90, 100, 110, 120, 150, 250, 300, 350, 380, 400, or more amino acids in length.

Variant proteins may include proteins that have at least about 80% amino acid sequence identity with a polypeptide sequence disclosed herein. Preferably, a variant protein will have at least about 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a polypeptide sequence as disclosed herein. Amino acid sequence identity is defined as the percentage of amino acid residues in the variant sequence that are identical with the amino acid residues in the reference sequence, after aligning the sequences and introducing gaps, if necessary, to achieve the maximum percent sequence identity, and not considering any conservative substitutions as part of the sequence identity. Sequence identity may be determined over the full length of both variant and reference amino acid sequences.

It will be understood by a skilled person that numerous different nucleic acids can encode the same polypeptide as a result of the degeneracy of the genetic code. In addition, it is to be understood that skilled persons may, using routine techniques, make nucleotide substitutions that do not affect the polypeptide sequence encoded by the nucleic acids of the invention to reflect the codon usage of any particular host organism in which the polypeptides are to be expressed. Nucleic acids encoding the ADI used in context of the invention may be modified by any method available in the art. Nucleic acids encoding the ADI used in context of the invention may be produced recombinantly, synthetically, or by any means available to those of skill in the art. They may also be cloned by standard techniques such as PCR (polymerase chain reaction).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

In the context of the present application, the percentage of identity is calculated using a global alignment (i.e. the two sequences are compared over their entire length). Methods for comparing the identity of two or more sequences are well known in the art. The "needle" program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix.

Proteins consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of deletions, insertions and/or substitutions, the protein consisting of an amino acid sequence at least 80%, 85%, 90%, 95%, 96%, 97%, 98% or 99% identical to a reference sequence may correspond to a homologous sequence derived from another species than the reference sequence.

Amino acid substitutions may be conservative or non-conservative. Preferably, substitutions are conservative substitutions, in which one amino acid is substituted for another amino acid with similar structural and/or chemical properties. The substitution preferably corresponds to a conservative substitution as indicated in table 1 herein below.

TABLE 1

Conservative amino acid substitution

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

Preferably, said variants or fragments retain a biological activity of a protein having the full-length amino acid sequence of SEQ ID NO 1.

In some embodiments, the arginine deiminase used in context of the invention might be a variant or fragment having an increased biological activity or enzymatic activity in comparison to a protein having the full-length amino acid sequence of SEQ ID NO 1. Accordingly, said variant or fragment might comprise amino acid substitutions that improve its enzymatic activity. "Improved enzymatic activity" herein refers, for example, to the improvement of the pH optimum, improvement of the Km and kcat values and an improved thermostability. Such mutations are either known to the skilled in the art or can be easily derived by the skilled in the art from the general knowledge as disclosed, for example, in Rui-Zhi Han et al. (Appl. Microbiol. Biotechnol. 2016, 100: 4747-4760).

In one embodiment, the arginine deiminase variant or fragment thereof might be modified in order to increase the plasma half-life in vivo.

Pharmaceutical Compositions or Suspensions

The terms "pharmaceutical composition" or "therapeutic composition" as used herein refer to a compound or composition capable of inducing a desired therapeutic effect when properly administered to a patient.

The invention refers to a pharmaceutical composition and a suspension, both comprising arginine deiminase encapsulated in erythrocytes. The definitions given in the present description refer to the compositions and the suspensions of the invention. The erythrocytes encapsulating ADI are preferably in suspension in a pharmaceutically acceptable vehicle.

"Pharmaceutically" or "pharmaceutically acceptable" refers to molecular entities and compositions that do not produce an adverse, allergic or other untoward reaction when administered to a mammal, especially a human, as appropriate.

According to a particular embodiment, the "pharmaceutically acceptable vehicle" is a "preservation solution" or a "preservative solution for erythrocytes", i.e. a solution in which the erythrocytes encapsulating the enzyme are suspended in their suitable form for being stored while awaiting their injection. A preservation solution preferably comprises at least one agent promoting preservation of the erythrocytes, notably selected from glucose, dextrose, adenine and mannitol.

In one embodiment, the preservation solution is an aqueous solution comprising NaCl and/or adenine. In a further embodiment, the preservation solution further comprises at least one compound selected from the group consisting of glucose, dextrose and mannitol. As an example, it may comprise NaCl, adenine and dextrose. In one example, the preservative solution is an AS3 medium. As another example, it may comprise NaCl, adenine, glucose and mannitol. In a further example, the preservative solution is a SAGM medium, such as SAG-Mannitol, or a ADsol medium.

The exact form of the pharmaceutical compositions, the route of administration, the dosage and the regimen naturally depend upon the condition to be treated, the severity of the illness, the age, weight, and gender of the patient, etc. It will be further understood that the composition and suspensions of the invention are intended for intravenous or intra-arterial administration, preferably for injection, infusion or perfusion. Accordingly, the pharmaceutical composition of the invention is formulated for intravenous or intra-arterial administration.

The compositions of the invention can be ready for use or not. The ready-for-use pharmaceutical composition of the invention has a hematocrit suitable for administration without dilution. When not ready for use, the composition can also be packaged with a higher hematocrit value such that it has to be diluted before administration.

The "hematocrit (Ht or HCT)" is generally known as the volume percentage (vol %) of red blood cells in blood. In context of the present invention, the hematocrit may further refer to the volume percentage (vol %) of red blood cells in the composition or suspension referred to, such as the pharmaceutical composition or the suspension of the erythrocytes.

According to the invention, the hematocrit of the ready-for-use pharmaceutical composition advantageously lies between 40 and 70%, preferably between 45 and 65%, more preferably between 45 and 55%, such as 46 and 54%, 47 and 53%, 48 and 52%, for example about 50%. When not ready-for-use the hematocrit of the to-be-diluted pharmaceutical composition can be higher, in particular lying between 50 and 90%, preferably 60 and 90%. In a connected embodiment, the dilution of the pharmaceutical composition to obtain the hematocrit values of the ready-to-use composition, defined herein above, may be made with the pharmaceutically acceptable vehicle.

"Erythrocytes" are also referred to as red blood cells. The erythrocytes develop in the bone marrow and circulate for about 100-120 days in the body before their components are recycled by macrophages. Nearly half of the blood's volume (40% to 45%) is red blood cells. Methods to isolate erythrocytes are known to the skilled in the art.

In one embodiment, the erythrocytes are issued from a mammal of the same species than the treated subject or patient. When the mammal is a human, the erythrocytes are preferably of human origin. In an embodiment, the erythrocytes come from the patient itself.

In another embodiment, stem cells are used to generate the erythrocytes. The person skilled may refer to Russeau et al. (ISBT Science Series (2016) 11 (Suppl. 1), 111-117). The stem cells may further be transformed to express the enzyme inside the erythrocytes. The person skilled in the art may further refer to US2015/0182588. These documents are incorporated herein by reference.

The arginine deiminase used in context of the invention is highly active. Activity may be expressed using, for example, the unit U. The "unit (U)" refers to the amount of enzyme that converts 1 µmole of substrate per minute. Accordingly, in context of the present invention 1U refers to the amount of enzyme that converts 1 µmole of arginine per minute, preferably, at 37° C. More preferably, 1U refers to the activity of the arginine deiminase when present in the buffers usually used for measuring the activity of arginine deiminase, such as the buffers specified in (Boyde and Rahmatullah, 1980, Analytical Biochemistry, vol 107, p424-431). In some embodiments, the "unit" as defined herein above may also be referred to as "international unit (IU)". Accordingly, in some embodiments 1U and 1 IU are interchangeable.

Methods to qualitatively and/or quantitatively evaluate the activity of an arginine deiminase are known to the skilled in the art. Typically, the activity of arginine deiminase is measured as described in detail herein below in the experimental section, in particular in example 1 and 2 of the experimental section. The exact experimental conditions used to measure the activity of arginine deiminase are known to the skilled in the art and for example described in (Boyde and Rahmatullah, 1980, Analytical Biochemistry, vol 107, p424-431). In one embodiment, the arginine deiminase used in context of the invention has, prior to encapsulation, a specific activity of 10 to 100 U/mg, such as 20 to 80, 30 to 70, 40 to 60 U/mg, wherein the mg refer to the amount of purified enzyme.

"Purified enzyme" herein refers to an enzyme having a purity of 90 to 100%, such as 92 to 100%, 94 to 100%, more than 96%, more than 97%, more than 98%, more than 99%, for example 97%. Methods to determine the purity of an enzyme are known to the skilled in the art and include, for example, SDS gel analysis, or Mass spectrometry analysis, preferably SDS gel analysis.

"Arginine deiminase is encapsulated into erythrocytes" means that the arginine deiminase is contained within the erythrocytes.

In one embodiment, the concentration of encapsulated arginine deiminase in context of the present invention, also referred to as intra-erythrocyte concentration of arginine deiminase, is from 0.1 to 7 mg/ml, preferably 0.5 to 6.5 mg/ml, such as 1 to 6 mg/ml, 1 to 5 mg/ml, 1 to 4 mg/ml, 1 to 3 mg/ml, more preferably, 1.2 to 2.8 mg/ml, 1.4 to 2.6 mg/ml, 1.6 to 2.4 mg/ml.

In some embodiments, the concentration of encapsulated arginine deiminase is at least 0.1, 0.2, 0.4, 0.6, 0.8, 1, 1.2, 1.4, 1.6, 1.8, 2, 2.2, 2.4, 2.6, 2.8, 3, 3.5, 4, 4.5, 6 mg/ml. In some embodiments, the concentration of encapsulated arginine deiminase is at most 7, 6.5, 5, 5.5, 5, 4.5, 4, 3.5, 3, 2.5, 2 mg/ml.

In another embodiment, the concentration of encapsulated arginine deiminase is from 1 to 1000 U/ml, preferably 1 to 500 U/ml, such as 1 to 400 U/ml, 5 to 400 U/ml, 5 to 350 U/ml.

In some embodiments, the concentration of encapsulated arginine deiminase is at least 0.5, 1, 2, 3, 4, 5, 10, 20, 30, 40, 50, 100, 200 to 400 U/ml. In some embodiments, the concentration of encapsulated arginine deiminase is at most 1000, 800, 600, 500, 400, 350, 300, 200, 100 U/ml.

Preferably, said concentration of encapsulated arginine deiminase, in mg/ml or in U/ml, refers to the intra-erythrocyte concentration of arginine deiminase per ml of the pharmaceutical composition of the invention or the suspension of the invention, more preferably, refers to the intra-erythrocyte concentration of the erythrocytes per ml of the erythrocyte solution of the composition or suspension, wherein said solution has typically a hematocrit of 50%.

In one embodiment, the composition or suspension of the invention, in a preservation solution, is characterized by an extracellular hemoglobin level maintained at a level equal to or less than 0.5, in particular 0.3, notably 0.2, preferably 0.15, even better 0.1 g/dl at 72 h and preservation at a temperature comprised between 2 and 8° C.

In particular, the composition or suspension of the invention, in a preservation solution, is characterized by an extracellular hemoglobin level maintained at a level equal to or less than 0.5, in particular 0.3, notably 0.2, preferably 0.15, even better 0.1 g/dl for a period comprised between 24 h and 20 days, notably between 24 and 72 h and preservation at a temperature comprised between 2 and 8° C.

The "extracellular hemoglobin level" is advantageously measured by the manual reference method described in G. B. Blakney and A. J. Dinwoodie, Clin. Biochem. 8, 96-102, 1975. Automatic devices also exist which allows this measurement to be made with a sensitivity which is specific to them.

In particular, the composition or suspension of the invention, in a preservation solution, is characterized by a hemolysis rate maintained at equal to or less than 2, notably 1.5, preferably 1% at 72 h and preservation at a temperature comprised between 2 and 8° C.

In particular, the composition or suspension, in a preservation solution, is characterized by a hemolysis rate maintained at equal to or less than 2, notably 1.5, preferably 1% for a period comprised between 24 h and 20 days, notably between 24 and 72 h and at a temperature comprised between 2 and 8° C.

In one embodiment, the composition of the invention is a suspension. In one embodiment, the suspension of the invention and the suspension in context of the invention have an osmolarity of between 270 and 350 mOsm/l. Methods to measure osmolarity are known to the skilled in the art. In one example, the osmolarity is measured with an osmometer (Micro-Osmometer Loser Type 15). The osmolarity is preferably measured at standard conditions (i.e. at 25° C. and 1 atm).

Therapeutic Methods and Uses

The inventors of the present invention have shown that a pharmaceutical composition comprising arginine deiminase encapsulated into erythrocytes decreases blood L-Arginine levels in arginase deficient mice by up to 73% three days after administration, for instance, when administered at a dose of 8 ml/kg. It will be understood by the skilled in the art that these results demonstrate that the composition of the invention, as well as the suspension of the invention may be used to treat arginase-1 deficiency, because the elevated level of serum arginine is directly related to clinical condition of the subject or patient which is treated.

The inventors further demonstrated in mice that surprisingly administering the composition or suspension of the invention does not notably changes ammonia levels in the treated mice and thus potentially does not affect eventual episodes of hyperammonemia in the subject or patient that is treated.

Accordingly, the present invention refers to a pharmaceutical composition comprising arginine deiminase encapsulated into erythrocytes and a pharmaceutically acceptable vehicle, for its use in treating arginase-1 deficiency. The invention further refers to a suspension of erythrocytes encapsulating arginine deiminase, in particular arginine deiminase from *M. arginini*, for its use in treating arginase-1 deficiency.

"Arginase-1 deficiency" is an inherited metabolic disease in which the body is unable to process arginine (a building block of protein). It belongs to a group of disorders known as urea cycle disorders. These occur when the body's process for removing ammonia is disrupted, which can cause ammonia levels in the blood to rise (hyperammonemia). In most cases, symptoms appear between the ages of one and three years. Symptoms may include feeding problems, vomiting, poor growth, seizures, and stiff muscles with increased reflexes (spasticity). People with arginase-1 deficiency may also have developmental delay, loss of developmental milestones, and intellectual disability. Arginase-1 deficiency is caused by mutations in the ARG1 gene and is inherited in an autosomal recessive manner. Most people with arginase-1 deficiency appear to be healthy at birth and have normal development during early childhood. The first features of arginase-1 deficiency often appear between the ages of one and three years. In some cases, symptoms may begin earlier or later.

Arginase-1 deficiency may be characterized by one or more signs and symptoms selected from the list including poor growth (present in all the people who have arginase deficiency), stiff muscles and increased reflexes (spasticity), developmental delay, loss of previously acquired developmental milestones, intellectual disability, seizures, small head size (microcephaly), problems with balance and coordination, behavioral abnormality, diaminoaciduria, Intellectual disability (severe), neurological speech impairment, EEG (Electroencephalogram) abnormality, hemiplegia/hemiparesis, hyperammonemia, progressive spastic quadriplegia and seizures.

"Methods to diagnose Arginine 1 deficiency" are known to the skilled in the art and usually include a full-panel expanded newborn screening testing. Typically, three- to fourfold elevation of plasma arginine concentration above the upper limit of normal is highly suggestive of the diagnosis. The diagnosis is further typically confirmed by identification of biallelic ARG1 pathogenic variants on molecular genetic testing or failure to detect arginase enzyme activity (usually <1% of normal) in red blood cell extracts.

The invention further refers to a method for treating arginase-1 deficiency comprising administering to a patient in need thereof an effective amount of arginine deiminase encapsulated into erythrocytes or an effective amount of the composition of the invention.

In the context of the invention, the term "treating" or "treatment", as used herein, means reversing, alleviating, inhibiting the progress of, or preventing the disorder or condition to which such term applies, or one or more symptoms of such disorder or condition.

Accordingly, the term "treatment" not only includes treatment leading to complete cure of the disease, but also treatments slowing down the progression of the disease and/or prolonging the survival of the patient.

An "effective amount" refers to an amount effective, at dosages and for periods of time necessary, to achieve the desired therapeutic or prophylactic result.

A therapeutically effective amount of the composition or suspension of the invention may vary according to factors such as the disease state, age, sex, and weight of the individual, and the ability of the protein, to elicit a desired therapeutic result. A therapeutically effective amount encompasses an amount in which any toxic or detrimental effects of the inhibitor are outweighed by the therapeutically beneficial effects. A therapeutically effective amount also encompasses an amount sufficient to confer benefit, e.g., clinical benefit.

In some embodiments, the methods of the invention comprise the administration of the composition of the invention as defined herein above, in combination with at least one further treatment which is directed against arginase-1 deficiency, either sequentially or simultaneously.

One further treatment directed against arginase-1 deficiency herein refers to low-protein diet, administration of nitrogen scavengers, injections of botulinum toxin, or the administration of amino acids such as ornithine or lysine.

"Nitrogen scavengers" include, but are not limited to, benzoate, phenylbutyrate, and phenylacetate.

As indicated herein above, the inventors of the present invention demonstrated that the arginine deiminase of *M. arginini* encapsulated in Erythrocytes decreases blood L-arginine levels in arginase-1 deficient mice by up to 73% three days after administration, for instance when administered at a dose of 8 ml/kg.

Accordingly, it will be understood by the skilled in the art that a pharmaceutical composition comprising a suspension of erythrocytes encapsulating arginine deiminase from *M. arginini* is not only efficient in the treatment of arginase-1 deficiency but also in the treatment of other diseases in which lowering the concentration of blood arginine might be beneficial.

Accordingly, the invention finds particularly interesting application in arginine-dependent cancers, for which the favorable effect of plasma arginine depletion has been demonstrated (see for example F. Izzo et al., 2004, C. M. Ensor et al., 2002, F. W. Holtsberg et al., 2002, J. S. Bomalaski et al., 2003, and Curley S. A. et al., 2003, previously cited).

However, plasma arginine depletion may also be beneficial for treating or preventing of septic shock, inhibition of angiogenesis and associated diseases.

Accordingly, in one embodiment, the present invention refers to a pharmaceutical composition comprising a suspension of erythrocytes encapsulating arginine deiminase from *M. arginini* for its use in lowering the concentration of blood arginine.

Accordingly, in a related embodiment, the present invention refers to a pharmaceutical composition comprising arginine deiminase from *M. arginini* encapsulated into erythrocytes and a pharmaceutically acceptable vehicle for its use in lowering the concentration of blood arginine The definitions referring to the "pharmaceutical compositions", the "arginine deiminase", "suspension", "pharmaceutically acceptable vehicle" are as given herein above and apply mutatis mutandis.

In particular, lowering the concentration of blood arginine is useful in treating arginase-1 deficiency, treating arginine-dependent cancers, treating or preventing a septic shock, for the inhibition of angiogenesis and the treatment of associated diseases.

Accordingly, in one embodiment, the invention refers to a pharmaceutical composition comprising a suspension of erythrocytes encapsulating arginine deiminase from *M. arginini* for its use in treating arginase-1 deficiency, treating arginine-dependent cancers, treating or preventing of septic shock, inhibition of angiogenesis and associated diseases.

Accordingly, in a related embodiment, the present invention refers to a pharmaceutical composition comprising arginine deiminase from *M. arginini* encapsulated into erythrocytes and a pharmaceutically acceptable vehicle for its use in treating arginase-1 deficiency, treating arginine-dependent cancers, treating or preventing of septic shock, inhibition of angiogenesis and associated diseases.

"Arginase-1 deficiency" is as defined herein above.

"Arginine-dependent cancers" refer to cancers involving cancer cells that require arginine for replication, those tumors are unable to synthesize some or all of the arginine that they need, mostly due to the lack of the biosynthetic enzyme asparagine synthetase and therefore require a supply of arginine, therefore those cancers are also referred to as "arginine auxotrophic cancers". Plasma arginine depletion will deprive these cells of the arginine that is essential for their development, leading to targeted death of these cells, inhibition of tumor growth or regression of the tumor mass.

Arginine dependent cancers may be selected from the group consisting of hepatocarcinoma, primary liver cancer, melanoma, breast cancer, neuroblastoma, leukemia, mesothelial cancer, urological cancer, sarcoma, gastric cancer and cerebral cancer.

"Mesothelial cancer" refers, for instance, to malignant pleural mesothelioma (MPM).

"Urological cancer" includes, for instance, renal cell carcinoma, prostate cancer, colon cancer and bladder cancer, in particular transitional cell carcinoma.

"Sarcoma" refers, for example, to Astrocytoma, Oligodendroglioma.

"Cerebral cancer" refers, for example, to osteosarcoma.

In one aspect, the arginine dependent cancer is hepatocarcinoma or primary liver cancer. In a further aspect, the arginine dependent cancer is melanoma, in particular, malignant melanoma, in its various forms, such as superficial spreading melanoma and nodular melanoma. According to a further aspect, the arginine dependent cancer is one of the following forms of cancer:

breast cancer,
neuroblastoma (Gong H. et al., Int. J. Cancer 2003, 106: 723-8),
leukemia (Gong H. et al. Leukemia 2000, Vol. 14, 826-9; Noh E. J. et al., Int. J. Cancer 2004, 112: 502-8).

"Treating" is as defined herein above.

By "preventing" or "Prevention" is meant a prophylactic use (i.e. on an individual susceptible of developing a given disease).

"Inhibition of angiogenesis and the treatment of associated diseases" refers to the treatment of diseases such as: angioma, angiofibroma, arthritis, diabetic retinopathy, retinopathy of the premature, neovascular glaucoma, disease of the cornea, involutional and other forms of macular degeneration, pterygium, retinal degeneration, retrolental fibroplasia, psoriasis, telangiectasia, granuloma pyogenicum, seborrheic dermatitis, acne, cancer and metastases connected with angiogenesis (WO0209741; Park I. S. et al., Br. J. Cancer 2003, 89: 907-14).

A further object of the invention is the use of erythrocytes encapsulating ADI or a suspension of such erythrocytes for the preparation of a medicament intended for the treatment of the diseases presented herein.

This use takes account of the characteristics presented for the suspensions and the pharmaceutical compositions of the invention or medicament.

Another object of the invention is a method for treating arginase-1 deficiency, comprising administering to a patient in need thereof an effective amount of the pharmaceutical composition of the invention or administering to a patient in need thereof an effective amount of arginine deiminase encapsulated into erythrocytes or administering to a patient in need thereof an effective amount of the medicament according to the invention.

Another object of the invention is a method for treating arginase-1 deficiency or arginine-dependent cancers, treating or preventing of septic shock, inhibiting angiogenesis or treating angiogenesis associated diseases comprising administering to a patient in need thereof an effective amount of the pharmaceutical composition comprising arginine deiminase from *M. arginini* or an effective amount of arginine deiminase from *M. arginini* encapsulated into erythrocytes or administering to a patient in need thereof an effective amount of the medicament according to the invention.

The method of treatment comprises the administration to a patient in need thereof of a "therapeutically effective dose," "therapeutically effective amount," or "effective amount", wherein an effective amount is as defined herein above.

In particular, a "therapeutically effective dose," "therapeutically effective amount," or "effective amount" can be routinely determined by those of skilled in the art. The amount of the enzyme actually administered may be determined by a physician, in the light of the relevant circumstances, including the condition to be treated, the chosen route of administration, the actual compound administered the age, weight, and response of the individual patient, the severity of the patient's symptoms, etc. The effective amounts may typically be sufficient to induce depletion of arginine in the blood circulation. Preferably, this depletion may correspond to maintaining arginine below a threshold level during a sufficient amount of time.

In some examples, the arginine level may be maintained below a threshold level for at least 1, 2, 3, 4, 5, 6, 7, 8, 9 10 days, preferably for at least 3 days.

Typical effective amounts of enzyme are further detailed herein below in the section "dose".

The pharmaceutical compositions can be administered by intravenous or intra-arterial injection and preferably by injection, infusion or perfusion from a blood bag or the like. Administration is typically affected intravenously into the arm or via a central catheter.

In particular, from about 10 to about 250 ml of suspension (one dose), pharmaceutical composition or medicament according to the invention is administered. Beyond 20 ml, use of infusion or perfusion is preferred.

A treatment comprises the administration of one dose or of several doses according to the protocol decided. This can provide for several administrations at monthly, fortnightly or weekly intervals, preferably once, twice or three times a week, over the recommended duration of the treatment.

In one embodiment, the treatment in context of the invention can consist in the administration of one dose, as defined herein below in the section dose, each time (each dose).

In one example, the treatment in context of the invention can consist in the administration of the equivalent of 0.001 mg/kg of enzyme per kg of body weight to 1000 mg/kg of enzyme per kg of body weight, preferably 0.01 mg/kg of enzyme per kg of body weight to 500 mg/kg of enzyme per kg of body weight, preferably, each time (each dose). Preferably, from 0.01 mg/kg of enzyme per kg of body weight to 200 mg/kg of enzyme per kg of body weight is administered, preferably, each time (each dose).

In a further example, as further specified herein below in the section dose, the treatment in context of the invention can consist in the administration of the equivalent of 10 U/kg of patient body weight and 100000 U/kg of enzyme per kg of body weight each time (each dose). Preferably, from 10 U/kg of patient body weight and 15000 U/kg of enzyme per kg of body weight each time (each dose). More preferably, from 500 U/kg of patient body weight and 3500 U/kg of enzyme per kg of body weight each time (each dose).

Doses

The compositions of the invention are preferably packaged at or presented in a volume containing a pre-determined quantity of active material calculated to produce the desired therapeutic effect. It will be understood by the skilled in the art, that volume or dose of the composition to be administered depends, for example, on the condition of the mammal intended for administration (e.g., weight, age, sex and health, concurrent treatment, if any, frequency of treatment), the mode of administration and the type of formulation.

In context of the present invention, the volume in which the composition for administration is packaged is also referred to as a dose. In one embodiment, said volume is from 10 to 250 ml.

Accordingly, the composition for administration is preferably packaged at or presented in one dose; preferably said dose has a volume as defined herein above. The packaging is preferably in a container, such as, for instance a blood bag of the type suitable for a blood transfusion and the like. The whole of the quantity of encapsulated enzyme corresponding to the medical prescription is preferably contained in said container. In other words, one dose of erythrocytes encapsulating a given amount of enzyme may be present in one container or pharmaceutical composition. In one embodiment, this one dose is intended to be fully administered to a patient in need thereof. In another embodiment, the administration may be achieved in a single dose or several doses.

The amount of enzyme encapsulated in one dose may be between 0.001 mg/kg of patient body weight and 1000 mg/kg of patient body weight. More preferably, the amount of enzyme encapsulated in one dose is between 0.01 mg/kg of patient body weight and 1000 mg/kg of patient body weight. Most preferably, the amount of enzyme encapsulated in one dose is between 0.01 mg/kg of patient body weight and 500 mg/kg of patient body weight. Most preferably, the amount of enzyme encapsulated in one dose is between 0.01 mg/kg of patient body weight and 200 mg/kg of patient body weight or between 0.01 mg/kg of patient body weight and 100 mg/kg of patient body weight.

In some embodiments, the amount of enzyme encapsulated in one dose is at least 0.001, 0.005, 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 35, 40, 45, 50 mg/kg of patient body weight. In some embodiments, the amount of enzyme encapsulated in one dose is at most 200, 150, 100, 80, 70, 60, 50, 45, 40, 35, 30, 25, 20, 25, 15, 10, 5, 1, 0.5, 0.1 mg/kg of patient body weight.

The amount of enzyme encapsulated in one dose may also be between 10 U/kg of patient body weight and 100000 U/kg of patient body weight. More preferably, the amount of enzyme encapsulated in one dose is between 10 U/kg of patient body weight and 80000 U/kg of patient body weight. Most preferably, the amount of enzyme encapsulated in one dose is between 10 U/kg of patient body weight and 50000 U/kg of patient body weight. Most preferably, the amount of enzyme encapsulated in one dose is between 10 U/kg of patient body weight and 5000 U/kg of patient body weight, 50 U/kg of patient body weight and 3500 U/kg of patient body weight, or between 50 U/kg of patient body weight and 3500 U/kg of patient body weight.

In some embodiments, the amount of enzyme encapsulated in one dose may also be of at least 10, 25, 50, 75, 100, 150, 200, 250, 300, 350, 400, 450, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000 UI/kg of patient body weight. In some embodiments, the amount of enzyme encapsulated in one dose may also be of at most 10000, 9500, 9000, 8500, 8000, 7500, 7000, 6500, 6000, 5500, 5000, 4500, 4000, 3500, 3000, 2500, 2000, 1500, 1000, 900, 800, 600, 500, 450, 400, 350, 300, 250, 200, 150, 100 U I/kg of patient body weight.

It will be understood by the skilled in the art, that the doses used for the administration can be adapted as a function of various parameters, and in particular as a function of the mode of administration used, of the relevant pathology, or alternatively of the desired duration of treatment.

A pharmaceutical composition comprising arginine deiminase encapsulated into erythrocytes and a pharmaceutically acceptable vehicle has been described in the prior art in context of the treatment of cancers. Adaptation of the dosages described in the above identified publications to the compositions of the invention for use in in treating arginase-1 deficiency are within the capabilities of the person skilled in the art.

Methods of Encapsulation

The Erythrocytes may be obtained as described herein above in the section "Pharmaceutical compositions".

Encapsulating the enzymes into erythrocytes may be performed using an erythrocyte suspension that is put into contact with a hypotonic liquid medium resulting in the opening of pores in the erythrocyte membrane. There exist three alternatives in the lysis-resealing technique, which are hypotonic dialysis, hypotonic preswelling and hypotonic dilution, all based on the difference in osmotic pressure between the inside and the outside of the erythrocytes. Hypotonic dialysis is preferred.

The suspension of erythrocytes encapsulating the enzyme is notably able to be obtained with the following method:

1—suspending a pellet of erythrocytes in an isotonic solution at a hematocrit level equal to or greater than 65%, cooling between +1 and +8° C., 2—a lysis procedure, at a temperature maintained between +1 and +8° C., comprising the passing of the suspension of erythrocytes at a hematocrit level equal or greater than 65% and of a cooled hypotonic lysis solution between +1 and +8° C., into a dialysis device, such as a coil or a dialysis cartridge (the cartridge is preferred);

3—an encapsulation procedure by adding, preferably gradually, the enzyme to be encapsulated (notably in a solution made up beforehand) into the suspension before or during lysis, at a temperature maintained between +1 and +8° C.; and 4—a resealing procedure conducted in the presence of an isotonic or hypertonic, advantageously hypertonic solution, at a higher temperature, notably comprised between +30 and +42° C.

In a preferred alternative, use may be done of the method described in WO-A-2006/016247 (EP 1 773 452; which is incorporated herein by reference.):

1—suspending a pellet of erythrocytes in an isotonic solution at a hematocrit level equal to or greater than 65%, cooling between +1 and +8° C., 2—measuring osmotic fragility from a sample of erythrocytes from this same pellet, 3—a lysis procedure, at a temperature maintained between +1 and +8° C., comprising the passing of the suspension of erythrocytes at a hematocrit level equal to or greater than 65% and of a hypotonic lysis solution cooled between +1 and +8° C., into a dialysis device, such as a coil or a dialysis cartridge (the cartridge is preferred); the lysis parameters being adjusted according to the osmotic fragility measured earlier; notably, depending on the measured osmotic fragility, the flow of the erythrocyte suspension passing into the dialysis device is adjusted or the osmolarity of the lysis solution is adjusted; and 4—a procedure for encapsulation by adding, preferably gradually, the enzyme to be encapsulated (notably in a solution made beforehand) in the suspension before and during lysis, at a temperature maintained between +1 and +8° C.; and 5—a resealing procedure conducted in the presence of an isotonic or hypertonic, advantageously hypertonic solution, at a higher temperature, notably comprised between +30 and +42° C.

Notably, for dialysis, the pellet of erythrocytes is suspended in an isotonic solution with a high hematocrit level, equal to or greater than 65%, and preferably equal to or greater than 70%, and this suspension is cooled between +1 and +8° C., preferably between +2 and +6° C., typically around +4° C. According to a particular method, the hematocrit level is comprised between 65 and 80%, preferably between 70 and 80%.

When it is measured, the osmotic fragility is advantageously measured on erythrocytes just before the lysis step, in the presence or in the absence, preferably in the presence of the enzyme to be encapsulated. The erythrocytes or the suspension containing them are advantageously at a temperature close to, or identical with the temperature selected for lysis. According to another advantageous feature of the invention, the conducted measurement of the osmotic fragility is rapidly utilized, i.e. the lysis procedure is carried out in a short time after taking the sample. Preferably, this lapse of time between the sampling and beginning of lysis is less than or equal to 30 minutes, still better less than or equal to 25 and even to 20 minutes.

As regards performing the lysis-resealing procedure with measurement and accounting for the osmotic fragility, one skilled in the art may refer for more details to WO-A-2006/016247. This document is incorporated herein by reference in its entirety.

An improvement of this encapsulation technique was described in WO 2014/180897, to which one skilled in the art may refer and which is incorporated herein by reference. Thus, according to an embodiment, the erythrocytes encapsulating the enzyme, are obtained by a method comprising the encapsulation of the active ingredient inside erythrocytes by lysis-resealing, the obtaining of a suspension or of a pellet comprising erythrocytes incorporating the enzyme and a solution with an osmolality greater than or equal to 280 mOsmol/kg, in particular between about 280 and about 380 mOsmol/kg, preferably between about 290 and about 330 mOsmol/kg, the incubation of the pellet or of the suspension as such or after adding an incubation solution, at an osmolality greater than or equal to 280 mOsmol/kg, in particular between about 280 and about 380 mOsmol/kg, preferably between about 290 and about 330 mOsmol/kg. Incubation is notably carried out for a period greater than or equal to 30 minutes, in particular greater than or equal to 1 h. It is then proceeded with removal of the liquid medium of the incubated solution and the erythrocytes obtained are suspended in a solution allowing injection of the suspension into a patient, preferably a preservation solution allowing injection of the suspension into a patient. The indicated osmolality is that of the solution in which the erythrocytes are suspended or in a pellet at the relevant moment.

By "stabilized erythrocyte suspension", is notably meant a suspension having an extracellular hemoglobin content which remains less than or equal to 0.2 g/dl until its use in humans, the latter may intervene notably from 1 to 72 hours after producing the erythrocyte batch incorporating the active ingredient.

By "ready-to-use stabilized erythrocyte suspension", is meant the stabilized suspension in a solution allowing injection into a patient, notably in a preservation solution. Its hematocrit is generally equal to or greater than 35%, 40% or 45%.

By "erythrocyte pellet", is meant a concentrate or concentration of erythrocytes collected after separating the erythrocytes of the liquid medium in which they were suspended previously.

The separation may be ensured by filtration or by centrifugation. Centrifugation is the means generally used for such a separation. A pellet comprises a certain proportion of liquid medium. Generally, the pellet has a hematocrit comprised between 70 and 85%.

By "incubation solution", is meant the solution in which the erythrocytes encapsulating an active ingredient are present during the incubation step. The incubation may be accomplished over a large range of hematocrits, notably between 10 and 85% of hematocrit.

By "fragile erythrocytes", are meant the erythrocytes stemming from the incorporation procedure which may, once suspended in a preservation solution, be lysed when the suspension is preserved between 2 and 8° C., notably after 1 to 72 h.

By "initial hematocrit", is meant the hematocrit before cell loss due to lysis of the fragile erythrocytes during incubation.

The method may notably comprise the following steps:
(a) encapsulation of the enzyme inside erythrocytes, comprising the putting of the erythrocytes into contact with a hypotonic medium (allowing opening of pores in the membrane of the erythrocytes), the contacting with the active ingredient (for allowing it to enter the erythrocytes), the resealing of the erythrocytes, notably by means of an isotonic or hypertonic medium, advantageously hypertonic,
(b) obtaining or preparing a suspension or pellet comprising erythrocytes incorporating the enzyme and a solution with an osmolality greater than or equal to 280 mOsmol/kg, in particular between about 280 and about 380 mOsmol/kg, preferably between about 290 and about 330 mOsmol/kg,
(c) incubating the pellet or the suspension of step (b) as such or after adding an incubation solution, at an osmolality greater than or equal to 280 mOsmol/kg, in particular between about 280 and about 380 mOsmol/kg, preferably between about 290 and about 330 mOsmol/kg, for a period greater than or equal to 30 minutes, notably greater than or equal to 1 h,
(d) removing the liquid medium of the incubated suspension of step (c),
(e) suspending the erythrocytes obtained under (d) into a solution allowing injection of the suspension into a patient, preferably a preservation solution allowing injection of the suspension into a patient.

According to a first method, the step following the encapsulation by lysis-resealing, notably step (b), includes at least 1 washing cycle, preferably 2 or 3 washing cycles, by dilution of the obtained suspension or pellet in the lysis-resealing step or step (a) in a solution, at an osmolality greater than equal to 280 mOsmol/kg, in particular between about 280 and about 380 mOsmol/kg, preferably between about 290 and about 330 mOsmol/kg, and then obtaining a pellet of erythrocytes or a suspension. This pellet or this suspension comprises erythrocytes incorporating the enzyme and a solution with an osmolality greater than or equal to 280 mOsmol/kg, in particular between about 280 and about 380 mOsmol/kg, preferably between about 290 and about 330 mOsmol/kg. The following steps, e.g. (c), (d) and (e) are then applied.

According to a second method, in the lysis-resealing step or step (a), resealing of the erythrocytes by means of an isotonic or hypertonic medium produces the suspension of erythrocytes which may then be subject to incubation, e.g. the suspension of step (b), in a solution with an osmolality greater than or equal to 280 mOsmol/kg, in particular between about 280 and about 380 mOsmol/kg, preferably between about 290 and about 330 mOsmol/kg. In other words, the lysis-resealing step or step (a) includes a step for resealing the erythrocytes wherein the suspended erythrocytes encapsulating the enzyme are mixed with an isotonic or hypertonic resealing solution, advantageously hypertonic, producing a suspension of erythrocytes with an osmolality greater than or equal to 280 mOsmol/kg, in particular between about 280 and about 380 mOsmol/kg, preferably between about 290 and about 330 mOsmol/kg. In this method, the incubation step or step (c) comprises incubation of the suspension stemming from the resealing. The incubation is carried out for a period greater than or equal to 30 minutes, notably greater than or equal to 1 h. The following steps, e.g. (d) and (e) are then applied.

The steps following the lysis-resealing, e.g. (b) to (e), are conducted under conditions resulting in the lysis of fragile erythrocytes, or of a majority of them, notably more than 50, 60, 70, 80 or 90%, or more. To do this, it is possible to act on the incubation period, the incubation temperature and on the osmolality of the solution in which the erythrocytes are suspended. The higher the osmolality, the longer the incubation time may be. Thus the lower the osmolality, the shorter may be the incubation in order to obtain the same effect. Also, the higher the temperature, the shorter the incubation time may be, and vice versa. One or several washing cycles will then allow removal of cell debris and extracellular hemoglobin, as well as the extracellular enzyme.

According to the invention, a washing cycle comprises the dilution of the suspension or pellet of erythrocytes, and then the separation between the erythrocytes and the washing solution. Preferably, a washing step comprises preferably 2 or 3 dilution-separation cycles. The separation may be achieved by any suitable means, such as filtration and centrifugation. Centrifugation is preferred.

Incubation is not limited by the hematocrit of the suspension. In this way, a suspension having an initial hematocrit generally comprised between 10 and 85%, notably between 40 and 80% may be incubated. This is rather referred to as a pellet from 70% and as a suspension below this value.

The removal step or step (d) aims at removing the liquid portion of the suspension or of the incubated pellet, in order to notably remove cell debris and the extracellular hemoglobin, as well as consequently the extracellular enzyme.

According to a first method for the removal step or step (d), separation, notably centrifugation is carried out, this being notably applicable to a suspension. This separation may be followed by one or several, for example 2 or 3, washing cycles, by dilution in an isotonic solution, and then separation, notably by centrifugation.

According to a second method for the removal step or step (d), dilution before separation notably centrifugation is carried out, this being applicable to a suspension or to a pellet. The dilution may notably be carried out with an isotonic washing solution or with a preservation solution.

The final step or step (e) consists of preparing the final suspension such that it may be administered to the patient, without any other treatment.

According to a first method for this step, a dilution of the erythrocyte pellet from the removal step or step (d) is carried out with the injection solution, notably the preservation solution.

According to a second method for this step, one or several cycles for washing the erythrocyte pellet stemming from the removal step or step (d) is carried out with the injection solution, notably the preservation solution, by dilution followed by separation. After washing, the erythrocytes are re-suspended in the injection solution, notably the preservation solution. The method of the invention may further comprise one, several or the totality of the following features:

the incubation step or step (c) is carried out at a temperature comprised between about 2 and about 39° C., over sufficient time for ensuring lysis of fragile erythrocytes;

the incubation step or step (c) is carried out at a low temperature, notably comprised between about 2 and about 10° C., in particular between about 2 and about 8° C., and lasts for about 1 h to about 72 h, notably from about 6 h to about 48 h, preferably from about 19 h to about 30 h;

the incubation step or step (c) is conducted at a higher temperature comprised between about 20 and about 39° C., notably at room temperature (25° C.±5° C.) and lasts for about 30 min to about 10 h, notably from about 1 h to about 6 h, preferably from about 2 h to about 4 h; it is possible to operate at an even higher temperature than room temperature, but this may have a negative impact on the cell yield, P50 and/or the 2,3-DPG content;

in the incubation step or step (c), the suspension is at an initial hematocrit comprised between 10 and 85%, notably between 40 and 80%; a pellet from separation, having for example a hematocrit between 70 and about 85%, or a diluted pellet having a hematocrit comprised between about 40 and 70% may be incubated;

the incubation step comprises stirring of the suspension;

the incubation step does not comprise any stirring;

as a solution for washing and/or incubation, a metered aqueous NaCl solution is used for obtaining the desired osmolality; as an example, a solution may thus comprise 0.9% of NaCl; this solution may also comprise, notably in addition to NaCl, glucose, notably glucose monohydrate, monosodium phosphate dihydrate, disodium phosphate dodecahydrate; as an example, a composition comprises: 0.9% of NaCl, 0.2% of glucose monohydrate, 0.034% of monosodium phosphate dihydrate, 0.2% of disodium phosphate dodecahydrate;

the washing in the final step or step (e) is carried out with the preservation solution;

the osmolality of the solution (liquid portion) in the ready-to-use suspension or which may be injected into the patient is comprised between about 280 and about 380 mOsmol/kg, preferably between about 290 and about 330 mOsmol/kg;

the hematocrit of the ready-to-use suspension or which may be injected into the patient is equal to or greater than 35%, 40% or 45%;

all the steps for washing and incubation are carried out with the preservation solution;

the washing solution of step (b) and/or the washing solution of step (e) and the preservation solution are of the same composition and comprise compound(s) promoting preservation of the erythrocytes;

the preservation solution (and the washing solution(s) or the incubation solutions if necessary) is an aqueous solution comprising NaCl, adenine and at least one compound from among glucose, dextrose and mannitol;

the preservation solution (and the washing or incubation solution(s) if necessary) comprises NaCl, adenine and dextrose, preferably an AS3 medium;

the preservation solution (and the washing or incubation solution(s), if necessary) comprise NaCl, adenine, glucose and mannitol, preferably a SAG-Mannitol or ADsol medium.

The methods according to the invention notably comprise the following step:

(a) encapsulating the enzyme inside erythrocytes, comprising the contacting with a hypotonic medium allowing opening of pores in the membrane of the erythrocytes, the contacting with the enzyme in order to allow its entry into the erythrocytes, the resealing of the erythrocytes by means of an isotonic or hypertonic medium. It should be noted that the enzyme may be present in the suspension of erythrocytes before the lysis of the latter, or further be added during lysis or after lysis, but always before resealing. In an embodiment of this step (a), the method comprises the following substeps:

(a1) having a suspension of erythrocytes at a hematocrit equal to or greater than 60 or 65%, (a2) measuring the osmotic fragility of the erythrocytes in this suspension, (a3) a procedure for lysis and internalization of the active ingredient(s), comprising the passing of the erythrocyte suspension into a dialysis device, notably a dialysis cartridge, counter to a lysis solution, adjusting the flow of the erythrocyte suspension or adjusting the flow rate of the lysis solution or adjusting the osmolarity of the lysis solution, depending on the osmotic fragility measured under (a2), (a4) a procedure for resealing the erythrocytes.

Definitions given herein above in the section "Arginine deiminase", "Pharmaceutical compositions" or "suspension", "Therapeutic use" and "dose", such as "erythrocytes", "hematocrit level", "Arginine deiminase" apply mutatis mutandis to the section "Methods of encapsulation".

Throughout the instant application, features described in one section are entirely applicable to other sections of the instant description. For instance, the description referring to "Arginine deiminase" as given in the section "Arginine deiminase" is entirely applicable to the section called "Pharmaceutical compositions or suspensions", the section called "Therapeutic methods and uses", the section "Therapeutic methods and uses", the section "Methods of encapsulation" and the section "dose".

Throughout the instant application, the term "and/or" is a grammatical conjunction that is to be interpreted as encompassing that one or more of the cases it connects may occur. For example, the wording "low-protein diet and/or nitrogen scavenger drugs" in the phrase "outcomes are usually poor with a low-protein diet and/or nitrogen scavenger drugs" indicates that outcomes are poor for individuals treated with either a low-protein diet or nitrogen scavenger drugs or a combination thereof, i.e. a low-protein diet and nitrogen scavenger drugs.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of"). Furthermore the indefinite article "a" or "an" does not exclude a plurality. The mere fact that certain measures are recited in mutually different dependent claims does not indicate that a combination of these measures cannot be used to advantage.

The invention will now be described in more details with reference to the following figures and examples. All literature and patent documents cited herein are hereby incorporated by reference. While the invention has been illustrated and described in detail in the foregoing description, the examples are to be considered illustrative or exemplary and not restrictive.

BRIEF DESCRIPTION OF THE SEQUENCES

SEQ ID NO: 1 shows the amino acid sequence of full-length arginine deiminase from *Mycoplasma arginini* as available from the NCBI database under accession number WP_004416214.1

FIGURES

FIG. 1: Schematic representation of the urea cycle showing the role of the enzymes (NAGS, CPS1, ASS1, ASL, ARG1, OTC) and the transporters (ORNT1 and citrin) in conversion of ammonia nitrogen in urea.

Figure 2:
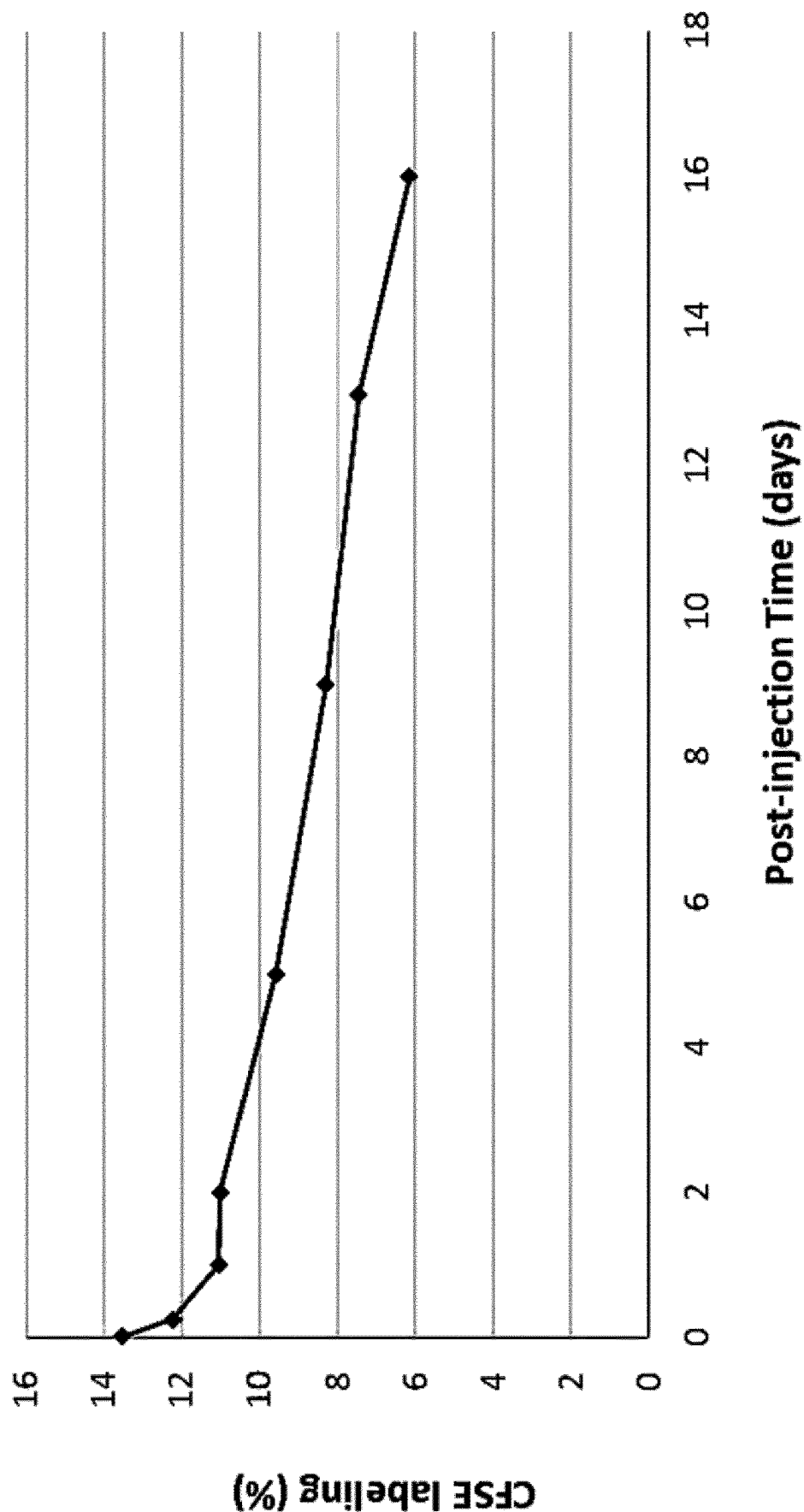

FIG. 2: Graph representing the Pharmacokinetics (PK) of CFSE-labeled erythrocytes encapsulating ADI. ERY-ADI 6 product is obtained by lysis-resealing of a suspension containing 5 mg/ml of ADI. Fluorescent labeling of the products (CFSE) allows traceability of the erythrocytes in vivo. The product injected intravenously to the mice C57BL/6 (8 ml/kg) has excellent stability with a half-life estimated between 18 and 22 days after their administration.

Figure 3:
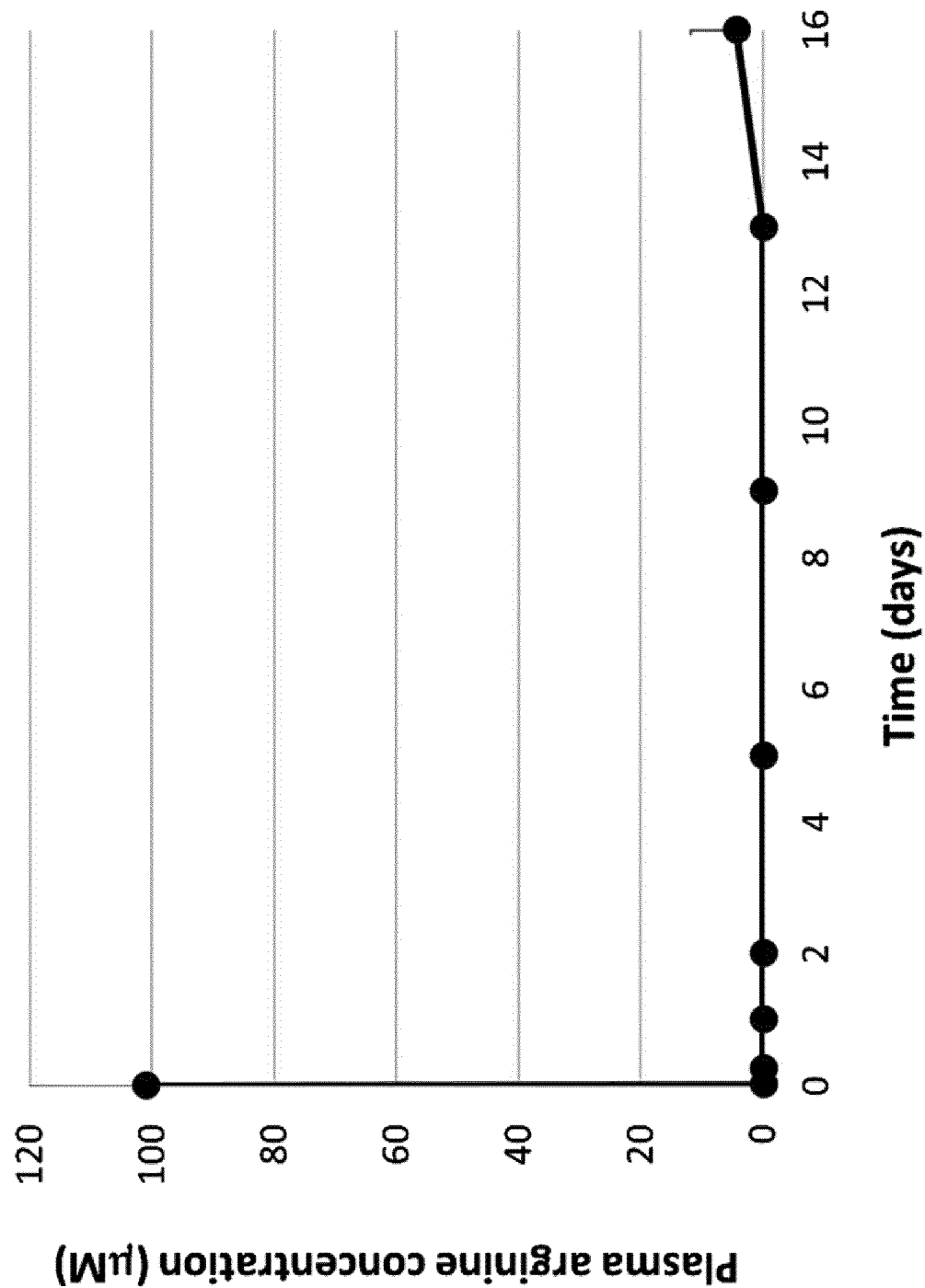

FIG. 3: Graph representing the Pharmacodynamics of erythrocytes encapsulating ADI over 16 days. The product ERY-ADI 6 is obtained by lysis-resealing of a suspension containing 5 mg/ml of ADI. The product is administered intravenously (IV) to C57BL/6 mice (8 ml/kg). The plasma L-arginine level is measured by HPLC-MS-MS. The L-Arginine level in untreated C57BL/6 mice was evaluated to be between 75 and 125 µM. The product ERY-ADI 6 leads to a rapid depletion 15 min after administration reducing the L-Arginine level to 0 µM for 13 days. On day 16, two out of three mice displayed a complete plasma L-arginine depletion. Plasma L-arginine of the third mouse was 13 µM. The average plasma L-arginine level for this group of mice at Day16 is 4.33±7.51 µM.

Figure 4:
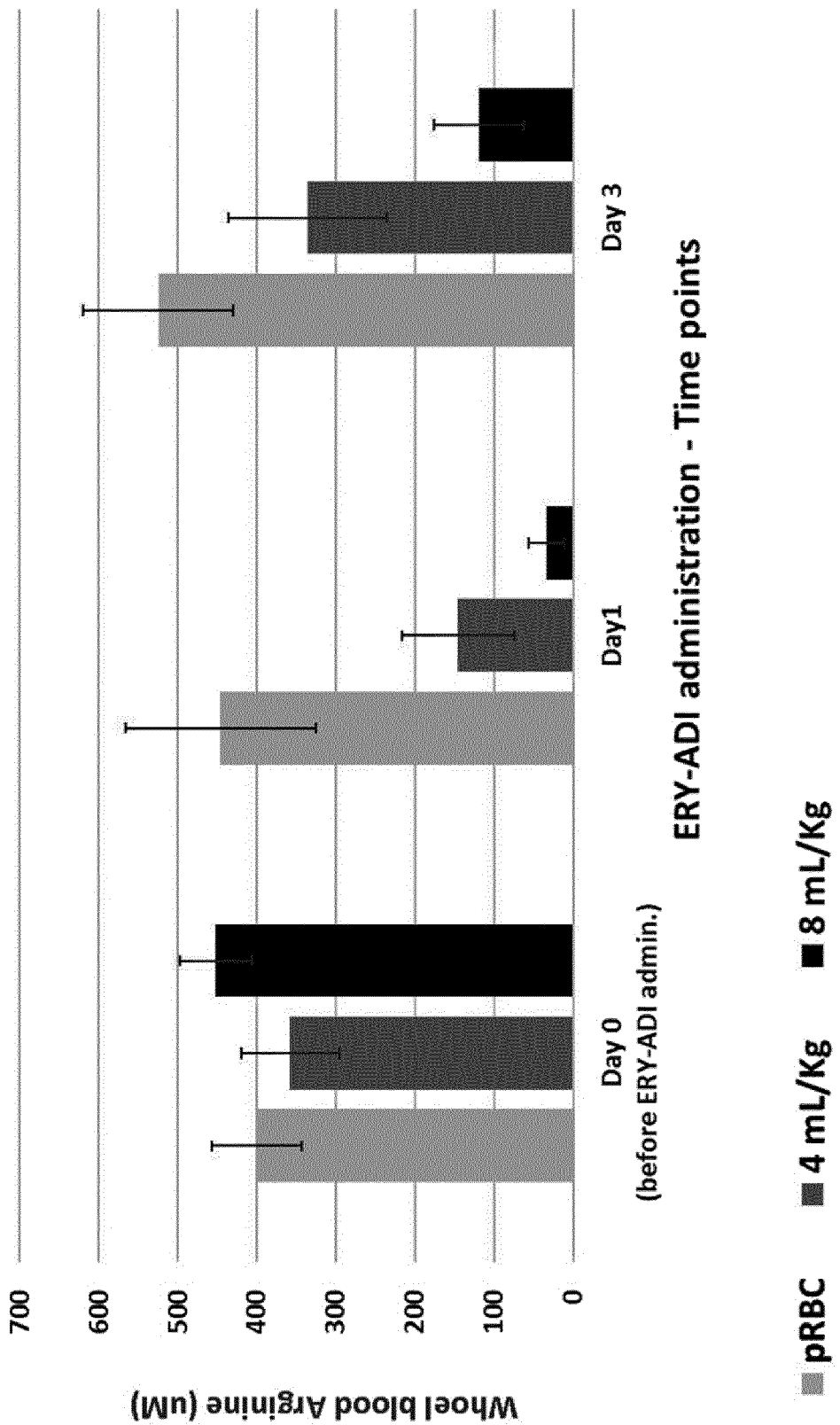

FIG. 4: Graph representing the blood L-Arginine level in arginase-deficient mice after one single intravenous administration of erythrocytes encapsulating ADI. The products ERY-ADI 4 is obtained by lysis-resealing of a suspension containing 4.5 mg/mL of ADI. As a control, a product named pRBC (Processed Red Blood Cells) has been obtained by lysis-resealing process without ADI enzyme (mock-loaded erythrocytes). On day 0, the two products are administered intravenously to arginase-deficient mice (4 or 8 mL/kg for ERY-ADI 4 and 8 mL/kg for pRBC). Blood sampling is performed on Day 0 (before ERY-ADI 4 or pRBC administrations) Day 1 and Day 3 for all mice. When ERY-ADI 4 was administered at 4 mL/kg, blood L-Arginine was lowered by 60% and by 7%, 1 and 3 days after injection, respectively. When double dose volume of ERY-ADI 4 was administered (8 mL/kg), the efficacy of erythrocytes encapsulating ADI on pathological blood L-Arginine level is spectacular; the following day after injection, the L-Arginine level is more that 10-fold lower than the L-Arginine concentration baseline of this mouse model (35±22 µM vs 452±45 µM corresponding to 92% blood depletion). Three (3) days after administration of ERY-ADI 4 product, blood L-Arginine level is still 4 times lower than the pathobiochemical level (119±57 µM vs 452±45 µM corresponding to 73% blood depletion). However, when mock-loaded erythrocytes (pRBC) were administered, no blood L-Arginine depletion has been observed. On the contrary, blood L-Arginine level still increased, demonstrating that mock-loaded erythrocytes had no effect on the biochemical course of the disease.

Figure 5:
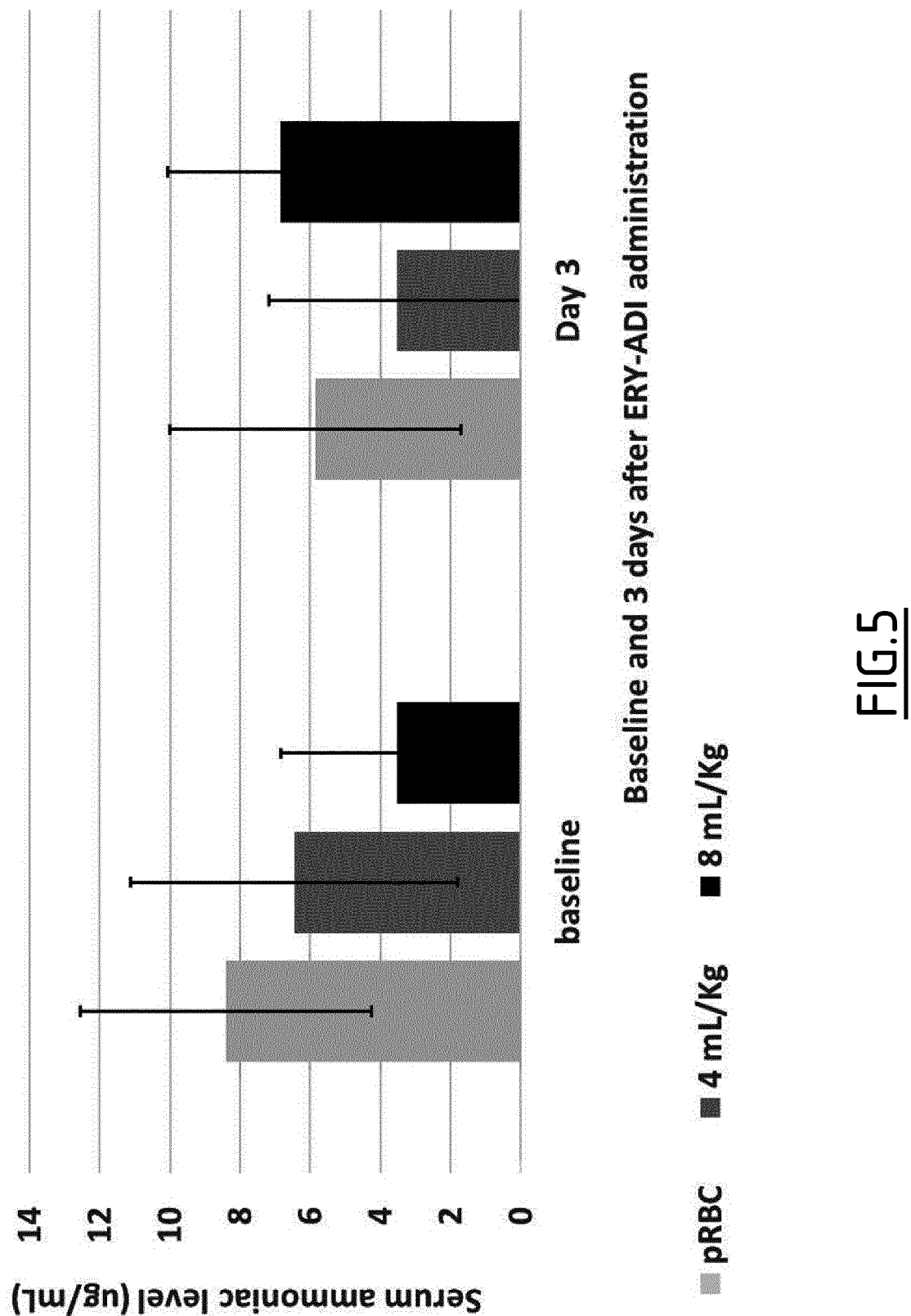

FIG. 5: Graph representing the serum Ammonia level in arginase-deficient mice after one single intravenous administration of erythrocytes encapsulating ADI. The products ERY-ADI 4 is obtained by lysis-resealing of a suspension containing 4.5 mg/mL of ADI. As a control, a product named pRBC (Processed Red Blood Cells) has been obtained by lysis-resealing process without ADI enzyme (mock-loaded erythrocytes). On day 0, the two products are administered intravenously to arginase-deficient mice (4 or 8 mL/kg for ERY-ADI 4 and 8 mL/kg for pRBC). Blood sampling is performed on Day 0 (before ERY-ADI 4 or pRBC administrations) and Day 3 for all mice to assay serum ammonia. Serum Ammonia was analyzed as the conversion of L-Arginine by ADI results in the production of Citrulline and Ammonia. No notable changes in ammonia levels have been observed when the mice were treated with erythrocytes encapsulating ADI or mock-loaded erythrocytes.

Figure 6:
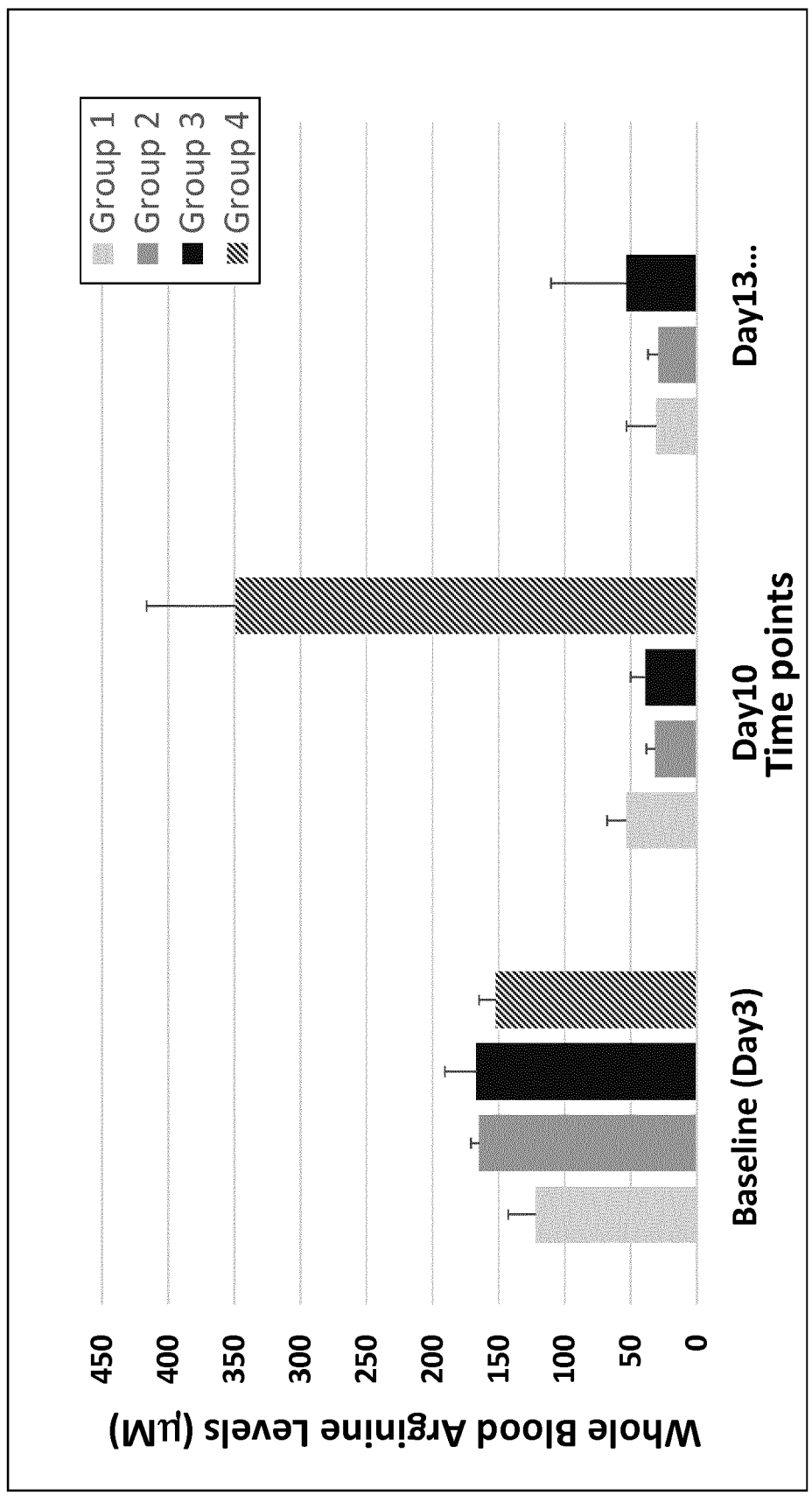

FIG. 6: Graph representing the blood L-arginine levels in arginase-deficient mice after administrations of ERY-ADI once (Group 2), twice (Group 3) or the free form of ADI enzyme (Group 4).

Figure 7:
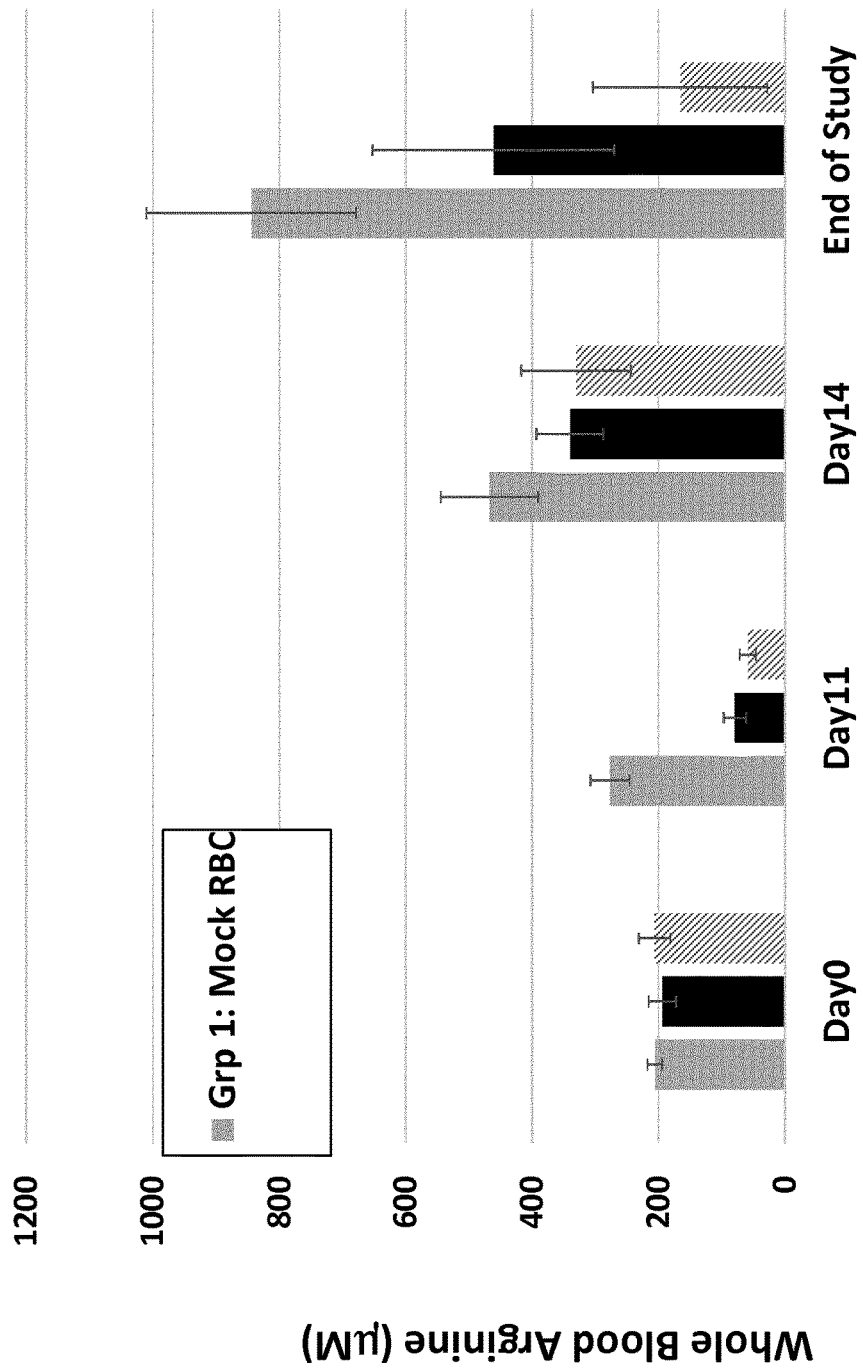

FIG. 7: Graph representing the blood L-arginine levels in arginase-deficient mice after administrations of Mock RBC (Group 1), ERY-ADI once (Group 2) and twice (Group 3).

EXAMPLES

Example 1. Method for Obtaining and Characterizing Arginine Deiminase (ADI)

Production of the strain and isolation of a hyper-producing clone: The natural sequence of ADI from *Mycoplasma arginini* (GenBank: X54141) was optimized by modifying some codons because genetic codes between *E. coli* and *M. arginini* are different (a new plasmid was created coded C1124-ADM-02). The purification process has been described in Misawa and coll. (Misawa, S. et al, 1994, J. of Biotechno. 36, 1994, 145-155) with some modifications, i.e., the bacterial production HMS174 (DE3) T1R strain has been used instead of the JM101 strain. Other modifications are described below.

Fermentation:

The production was achieved in a fermenter with FED_Coli_9 batch medium, with stirring, controlled pressure and pH from the pre-culture 2 at an optical density of 0.05. The growth phase (at 37° C.) took place until an optical density (600 nm) of 100 was obtained and the expression induction was achieved at 32° C. by adding 1 mM IPTG into the culture medium. The cell sediment was harvested 26-27 h after induction in two phases: the cell broth was concentrated 5-10 times after passing over a 500 kDa hollow fiber and then the cell pellet was recovered by centrifugation at 15900×g and then stored at −20° C.

Purification: ADI was produced as inclusion bodies (IB). The cell pellets were suspended in a lysis buffer to disrupt the cells. Then the disrupted cells were washed to collect the IBs and the IBs were stored at −20° C.

The purification of ADI started by thawing the IB pellet in a buffer composed of 50 mM TRIS base pH 8.5, 6M Guanidinium Hydrochloride, 10 mM Dithiothreitol. The solubilization was achieved with an incubation time of 1 h at 37±2° C. After clarification, the refolding step took place for 40-45 hours at room temperature in a buffer composed of 3 mM monopotassium phosphate (KH2PO4), 7 mM dipotassium phosphate (K2HPO4) pH 7.35. After a second clarification step, the medium was loaded onto a Q-sepharose column. Elution was performed with 250 and 500 mM NaCl and the elution fraction was submitted to a tangential flow filtration (TFF). Two polishing steps (using Sartobind Q column) and two TFF steps complete the purification of ADI. A final 0.2 µM filtration was performed before storage of ADI at −20° C.

Characterization: The specific activity of the enzyme was determined by measuring the produced Citrulline as described in example 2. The protein content was determined by reading absorbance at 280 nM. The purity was determined by SDS-PAGE. The osmolarity was measured with an osmometer (Micro-Osmometer Loser Type 15). The main characteristics of one produced batch of ADI are summarized herein below in table 2.

TABLE 2

Main characteristics of one produced batch of ADI

| | ADI of *M. arginini* |
|---|---|
| Formulation | Liquid phase frozen at −80° C.<br>Characteristics:<br>323 mOsm/Kg - 16.65 mg/mL<br>50 mM phosphate de sodium pH 6.5, Sucrose 40 mg/mL, Lysine 40 mM |
| Specific activity | ~47 U/mg |
| Purity | 97.5% |

Example 2. ADI Specific Activity Assay Using Citrulline Measurement

This assay is based on a 2-step reaction (Boyde and Rahmatullah, 1980, Analytical Biochemistry, vol 107, p 424-431):

First, L-Arginine is converted into citrulline and ammonia by ADI

Second, in presence of diacetyl monoxime, iron (III) chloride, thiosemicarbazide, sulfuric and phosphoric acids, citrulline is converted into a colored chromophore readable at 530 nm.

A L-citrulline standard curve is prepared to determine the ADI enzymatic activity of all assay samples, by reading the absorbance at 530 nm. Specific activity (U/mg) is calculated using the enzymatic activity (U/mL) and the protein content (mg).

Example 3. Encapsulation of ADI in Murine Erythrocytes

Whole blood of C57BL/6 mice (Charles River) was centrifuged at 1000×g, for 10 min, at 4° C. to remove the plasma and buffy coat. The erythrocytes were washed three times with 0.9% NaCl (v:v). The frozen ADI was thawed and added to the erythrocyte suspension in order to obtain a final suspension with a hematocrit of 65%, containing an initial concentration of ADI of 2 to 7 mg/mL.

The suspension was then loaded on a hemodialyzer at a flow rate of 120 ml/h and dialyzed against a hypotonic solution (40-50 mOsmol/kg) at a flow rate of 15 ml/min as a counter-current. The suspension was then resealed with a hypertonic solution (1 600-2 100 mOsmol/kg) and then incubated for 30 min at 37° C. After three washes in 0.9% NaCl, 0.2% glucose, the suspension was taken up in a preservation solution AS3 supplemented with 20% decomplemented plasma.

The obtained products are characterized at the time point D0 (within the 2 h following their preparation) and at time point D1 (i.e. after ~18 h-24 h of storage at 2-8° C.). The hematologic characteristics are obtained with a veterinary automaton (Sysmex, PocH-100iV).

Results:

ADI activity in the finished products was assayed with the method described in example 4 against an external calibration range of ADI in aqueous solution. These results show that ADI activity in the finished products increases with the amount of enzyme introduced into the RBC and that it is easily possible to encapsulate up to 2 mg of ADI per ml of finished product while maintaining good stability. The main characteristics of 6 different batches of ERY-ADI murine final products (ERY-ADI-1 to 6) are given herein below in Table 3.

TABLE 3

Main characteristics of 6 ERY-ADI murine final products as measured at the time point D 0 (2 h following the preparation)

| | Batches | ERY-ADI-1 | ERY-ADI-2 | ERY-ADI-3 | ERY-ADI-4 | ERY-ADI-5 | ERY-ADI-6 |
|---|---|---|---|---|---|---|---|
| Hematological parameters | Hematocrit (%) | 51.1 | 51.1 | 50.8 | 51.3 | 51.1 | 51.3 |
| | Corpuscle volume (fl) | 39.5 | 40.1 | 40.6 | 41.3 | 40.0 | 38.60 |
| | Corpuscle hemoglobin (g/dl) | 26.6 | 26.3 | 25.3 | 26.7 | 28.2 | 25.7 |
| | Total hemoglobin (g/dl) | 14.8 | 14.4 | 14.0 | 14.8 | 15.6 | 13.8 |
| | Extracellular Hb (g/dl) | 0.3 | 0.4 | 0.3 | 0.8 | 0.3 | 0.3 |
| ADI parameters | ADI concentration before process (mg/mL) | 3 | 4.5 | 4.5 | 4.5 | 3.5 | 5 |

TABLE 3-continued

Main characteristics of 6 ERY-ADI murine final products as measured at the time point D 0 (2 h following the preparation)

| Batches | ERY-ADI-1 | ERY-ADI-2 | ERY-ADI-3 | ERY-ADI-4 | ERY-ADI-5 | ERY-ADI-6 |
|---|---|---|---|---|---|---|
| Intra-erythrocyte concentration of ADI (mg/ml of RBC - 100% Ht) | 1.15 | 1.56 | 1.90 | 1.13 | 1.37 | 2.70 |
| Extracellular activity (%) | 4.8 | 5.7 | 4.8 | 6 | 4.0 | 4.1 |
| Intracellular activity (%) | 95.2 | 94.3 | 95.2 | 94 | 96.0 | 95.9 |
| Encapsulation yield of ADI (%) | 38 | 35 | 42 | 25 | 39 | 54 |

Example 4. Assay of Encapsulated ADI in the Erythrocytes

The assay of the ADI activity entrapped in red blood cells and in the supernatants, is based on a measurement of $NH_3$ produced by ADI from L-Arginine. The $NH_3$ ions were assayed indirectly by enzymatic action of glutamate dehydrogenase (GLDH) according to the kit marketed by Roche Diagnostics (11877984).

Example 5. Pharmacokinetics of Erythrocytes Encapsulating ADI in C57BL/6 Mice The murine product ERY-ADI 6 was labeled with CFSE (fluorescent) and administered intravenously into C57BL/6 mice. At each time points (D0+15 min, D0+6 h, D1, D2, D5, D9, D13 and D16), 3 mice were sacrificed and the blood was collected on a lithium heparinate tube kept at +4° C. away from light for determining the pharmacokinetics. The proportion of red blood cells labeled with CFSE in the whole blood was determined by a flow cytometry method. Five microliters of whole blood were diluted in 1 ml of PBS 0.5% BSA and each sample was passed in triplicate (counting of 10,000 cells in FL-1; cytometer FC500, Beckman Coulter). The evaluation of the survival of red blood cells loaded with ADI was obtained by adding the proportion of erythrocytes loaded with ADI labeled with CFSE at different time points to the proportion of erythrocytes loaded with ADI labeled with CFSE at T0+15 min (100% control). The different obtained percentages for each time are indicated in the graph depicted in FIG. 2 thus illustrating the proportion of erythrocytes loaded with ADI in circulation versus time.

Based on half-life calculation, CFSE-labeled erythrocytes encapsulating ADI have an estimated half-life comprised between 18 and 22 days.

Example 6. Pharmacodynamics of Erythrocytes Encapsulating ADI in C57BL/6 Mice The product ERY-ADI 6 of erythrocytes encapsulating ADI enzyme was injected intravenously to C57BL/6 mice at a dose of 8 ml/kg. At each time points (D0+15 min, D0+6 h, D1, D2, D5, D9, D13 and D16), 3 mice are sacrificed and the blood is collected on lithium heparinate tubes stored at 4° C. for the determination of plasma L-Arginine levels.

As shown in FIG. 3 a complete plasma L-Arginine depletion is observed for 13 days immediately (i.e. 15 minutes) after administration of erythrocyte encapsulating ADI. At the last time point of the study (i.e. 16 days), 2 mice out of 3 still displayed a complete plasma L-Arginine depletion. Plasma L-Arginine level of the third mouse was 13 µM, much lower than the physiological plasma L-Arginine concentration in this study (100±25 µM).

Example 7. Administration of Erythrocytes Encapsulating ADI to Arginase-Deficient Mice (1$^{st}$ Study)

An in vivo study was set up with an arginase-deficient mouse model (For a complete description see Sin et al, 2013, PLOS One, vol. 8 (11)). These mice are devoid of arginase 1 activity and exhibit severe pathobiochemical aspects of hyperargininemia commonly seen in humans. Hyperargininemia (or Arginase deficiency) is triggered by 5 injections of tamoxifen. Blood arginine concentrations start to rise few days after the last tamoxifen injection. To demonstrate an efficacy of murine product ERY-ADI 4 to decrease blood L-Arginine level in this mouse model, ERY-ADI 4 (4 and 8 mL/kg) and mock-loaded erythrocytes (8 mL/kg) were intravenously injected to 15 arginase-deficient mice 7 days after the last tamoxifen injection. Blood was collected the day (D1) and two days later (D3) after administration of the three products. Results of the in vivo study are presented in FIGS. 4 and 5 and in Table 4 below.

TABLE 4

Summary of the results of the in vivo study of ERY-ADI-4 in an arginase-deficient mouse model. Indicated are the % depletion of blood Arginine levels. Negative numbers indicate an increase of Arginine levels.

| % depletion (Blood L-Arg) | Mock loaded erythrocytes (8 mL/kg) | ERY-ADI 4 (4 mL/kg) | ERY-ADI 4 (8 mL/kg) |
|---|---|---|---|
| D1 | −10% | 60% | 92% |
| D3 | −30% | 7% | 73% |

As shown in this table and in FIG. 4, erythrocytes encapsulating ADI, when administered at a dose volume of 4 mL/kg, decreased blood L-Arginine by 60% and by 7%, 1 and 3 days after injection, respectively. When double dose volume was administered (8 mL/kg), the efficacy of erythrocytes encapsulating ADI on pathological blood L-Arginine level is spectacular; the following day after injection, the L-Arginine level is more that 10-fold lower than the L-Arginine concentration baseline of this mouse model (35±22 µM vs 452±45 µM corresponding to 92% blood depletion). Three (3) days after administration of ERY-ADI 4 product, blood L-Arginine level is still 4 times lower than the pathobiochemical level (119±57 µM vs 452±45 µM corresponding to 73% blood depletion). However, when mock-loaded erythrocytes were administered, no blood L-Arginine depletion has been observed. On the contrary, blood L-Arginine level still increased, demonstrating that mock-loaded erythrocytes had no effect on the biochemical course of the disease.

Serum Ammonia was analyzed at the same time as the conversion of L-Arginine by ADI results in the production of Citrulline and Ammonia. As shown in FIG. 5, no notable changes in ammonia levels have been observed when the mice were treated with erythrocytes encapsulating ADI or mock-loaded erythrocytes.

Example 8. Administration of Erythrocytes Encapsulating ADI to Arginase-Deficient Mice (Second Study)

To confirm the efficacy of murine product ERY-ADI to decrease blood L-Arginine level in this mouse model, a second study was set up on mice treated with tamoxifen in accordance with example 7. ERY-ADI product was intravenously injected 3 days after the last tamoxifen injection. One or two intravenous administration(s) of ERY-ADI (at 8 mL/kg) was scheduled (Groups 2 and 3 respectively). A control group was administered the free form of ADI enzyme (Group 4). A second control group composed of mice bearing arginase activity was part of the study (Group 1).

Blood was collected the day (D3) and one week later (Day10). The day of sacrifice, mice blood was collected too (Day 13).

Results of the second in vivo study are presented in FIG. 6.

First, blood arginine levels were lower in this second study because we changed the injections schedule related to the tamoxifen injections. In this study, the administration of ERY-ADI was planned 3 days instead of 7 days after last tamoxifen injection, resulting in a lower blood arginine level baseline.

As shown in FIG. 6, erythrocytes encapsulating ADI, when administered at a dose volume of 8 mL/kg, decreased blood L-Arginine by 81% and 77% compared to baseline levels for groups 2 and 3 respectively at Day 10 (i.e. 7 days after administration). The second administration of ERY-ADI was scheduled after the blood collection on day 10. Ten (10) days after administration, depletion of blood arginine is still very important with some percentages of depletion of 82% and 68% for group 2 and group 3 respectively compared to baseline levels. In contrast no blood arginine depletion was observed in mice injected with free form of ADI at Day 10 (Group 4). On the contrary the blood arginine concentration reached a concentration of 349 µM reflecting the blood arginine level increase in the model of arginase-deficient mice. No measurement of blood L-Arginine level could be performed at Day 13 for group 4 since all animals died further to the $2^{nd}$ injection with free form of ADI.

This second study confirmed the results observed with the first study with some additional information about the pharmacodynamics of the ERY-ADI product when injected to arginase-deficient mice. One single administration allows a blood arginine depletion for at least 10 days and a second injection of ERY-ADI product did not result in any side effects on this mouse model.

Example 9. Administration of Erythrocytes Encapsulating ADI to Arginase-Deficient Mice (Third Study)

As no survival was observed when ERY-ADI administration was performed 3 days after the last tamoxifen injection, the third study was designed with an important change in test item administration schedule. ERY-ADI was intravenously injected the day before the first tamoxifen injection (Day 0).

In this study, the last tamoxifen injection was carried out on Day 5. One or two intravenous administration(s) of ERY-ADI was scheduled (Groups 2 and 3, respectively). Group 1 was a control group composed of Arginase-deficient mice administered the mock RBC (i.e. processed RBC with no ADI). Blood was collected on Day 0, Day 11, Day 14 (before second administration of ERY-ADI) and when mice were sacrificed for excess body weight loss (identified as "end of study").

As shown in FIG. 7, erythrocytes encapsulating ADI, when administered at a dose volume of 8 mL/kg, decreased blood L-Arginine by 71.4% and 78.7% compared to group 1 levels for groups 2 and 3 respectively at Day 11 (i.e. 11 days after administration). At Day 14, before the second administration of ERY-ADI (for group 3 only), whole blood arginine was still depleted by 27.3% and 29.3% for groups 2 and 3 respectively, compared to group 1. In contrast, no whole blood arginine depletion was observed in mice injected with mock RBC (Group 1). In this group, the whole blood arginine concentration reached a concentration of 844 µM at the end of the study reflecting a whole blood arginine level increase in this arginase-deficient mouse model.

When ERY-ADI was reinjected at Day 14 (group 3), whole blood arginine level was measured few days later, at the time of sacrifice for ethical reasons (identified as "end of study"). The blood arginine was still depleted following the second administration of ERY-ADI, but arginase-deficient mice has to be sacrificed due to significant body weight loss.

This third study confirmed the results observed with the first two studies with some additional information about the pharmacodynamics of the ERY-ADI product when injected into arginase-deficient mice. A single administration yielded a blood arginine depletion for at least 11 days in this mouse model and a second injection of ERY-ADI yielded a sustained blood arginine depletion for at least 17 days (lifespan of the first mouse that had been sacrificed for ethical reasons).

However, due to the severity of this mouse model, no survival has been observed beyond 15 days after last tamoxifen injection, whatever the number of ERY-ADI administrations performed.

Example 10: Production of Human Red Blood Cells Encapsulating Arginine Deiminase A pouch of leucocyte-depleted human RBCs (provided by the "Etablissement frangais du sang") was subjected to three washes with 0.9% NaCl. The Arginine Deiminase (ADI) solution was gently thawed and added to the RBC suspension to obtain a final concentration with a hematocrit of 60% containing 3 or 5 mg/mL of ADI. The suspension was homogenized and loaded on a hemodialyzer at a flow rate of 90 mL/h and dialyzed against a hypotonic solution at 30 mOsmol/kg. The suspension was then resealed with a hypertonic solution and then incubated for 30 minutes a 30° C. After 3 washes in 0.9% NaCl, 0.2% Glucose, the suspension was taken up in a preservative solution AS3 (NaCl, $NaH_2PO_4$, Citric acid, Na-citrate, adenine and glucose. Osmolality is 288 mOs/kg and pH 5.88). The products obtained were characterized at Day 0, Day 1 and Day x. The hematologic characteristics were obtained with a veterinary automat (Sysmex, PocH-100iV).

It is important to note that no magnesium, iron or other enzyme co-factor was (or need be) added to the disclosed RBC-encapsulated arginine deiminase (ADI) compositions and suspensions. Unlike non-encapsulated ADI preparations, which may make use of magnesium or other co-factors present in a subject's bloodstream, the ADI of the present disclosure is generally limited to the contents of the RBCs. To solve this problem, Applicants specifically selected a co-factor-independent ADI (e.g. *M. arginine*) to ensure long-lasting in vivo ADI activity, without the need to supplement the products with magnesium or some other co-factor.

Applicants envision that other co-factor-independent ADI may be used effectively in the practice of the disclosed invention.

As used herein, "Co-factor-independent ADI" means an ADI that does not depend upon enzyme co-factors such as vitamins, pro-vitamins, vitamin precursors, or metal ions (e.g. magnesium, iron, manganese, etc.). As used herein, "magnesium-independent ADI" means an ADI that does not depend upon magnesium to support its enzymatic activity.

Results. The hematologic and biochemical characteristics of 6 finished products at Day 0 (day of manufacturing) are compiled in Table 5 below: three were manufactured with an ADI concentration of 3 mg/mL and three with an ADI concentration of 5 g/mL, expressed with respect to the RBC suspension before dialysis. All the ERY-ADI products were prepared with the same batch of ADI. In vitro stability was assessed on Day 0, Day 1 (Table 6) and Day 7 (Table 7).

TABLE 5

Hematologic and biochemical characteristics of ERY-ADI I to VI (Day 0)

| | | ADI 3 mg/mL | | | ADI 5 mg/mL | | |
|---|---|---|---|---|---|---|---|
| | Day 0 parameters | ERY-ADI I | ERY-ADI II | ERY-ADI III | ERY-ADI IV | ERY-ADI V | ERY-ADI VI |
| Hemato-Logical data | Hematocrit (%) | 48.2 | 50.8 | 48.0 | 50.4 | 48.0 | 49.2 |
| | Corpuscular volume (fL) | 87.5 | 82.9 | 85.7 | 85.3 | 83.3 | 86.9 |
| | Corpuscular hemoglobin (g/dL) | 27.6 | 28.6 | 28.6 | 28.1 | 29.4 | 27.9 |
| | RBC count ($10^6/\mu L$) | 5.52 | 6.12 | 5.60 | 5.92 | 5.78 | 5.66 |
| | Total Hemoglobin (g/dL) | 13.4 | 14.4 | 13.8 | 14.2 | 14.2 | 13.8 |
| | Extracellular Hb (g/dL) | 0.1 | 0.1 | 0.1 | 0.1 | 0.1 | 0.1 |
| ADI | Intra-erythrocyte concentration of ADI (mg/mL of RBC) | 0.88 | 0.94 | 1.01 | 1.55 | 1.36 | 1.46 |
| | Intra-erythrocyte activity of ADI (U/mL) | 42.1 | 44.9 | 48.3 | 74.1 | 65.0 | 69.8 |
| | Extracellular activity (%) | 1.2 | 0.0 | 3.0 | 0.6 | 0.8 | 4.0 |
| | Intracellular activity (%) | 98.8 | 100.0 | 97.0 | 99.4 | 99.2 | 96.0 |
| | Entrapment yield of ADI (%) | 29.4 | 31.5 | 33.7 | 31.0 | 27.3 | 29.3 |

Independent of the ADI concentration added before entrapment, the entrapment yield was very reproducible (from 27.3 to 33.7%).

TABLE 6

Hematologic and biochemical characteristics of ERY-ADI I to VI (Day 1)

| | | ADI 3 mg/mL | | | ADI 5 mg/mL | | |
|---|---|---|---|---|---|---|---|
| | Day 1 parameters | ERY-ADI I | ERY-ADI II | ERY-ADI III | ERY-ADI IV | ERY-ADI V | ERY-ADI VI |
| Hemato-Logical Data | Hematocrit (%) | 46.6 | 51.4 | 47.8 | 49.4 | 49.0 | 46.4 |
| | Corpuscular volume (fL) | 85.5 | 81.6 | 83.8 | 83.8 | 81.4 | 84.7 |
| | Corpuscular hemoglobin (g/dL) | 28.8 | 30.3 | 29.1 | 28.3 | 29.6 | 29.1 |
| | RBC count ($10^6/\mu L$) | 5.46 | 6.28 | 5.70 | 5.90 | 6.02 | 5.48 |
| | Total Hemoglobin (g/dL) | 13.4 | 15.6 | 14.0 | 14.0 | 14.4 | 13.4 |
| | Extracellular Hb (g/dL) | 0.1 | 0.1 | 0.2 | 0.1 | 0.1 | 0.2 |
| ADI | Intra-erythrocyte concentration of ADI (mg/mL of RBC) | 0.89 | 0.83 | 1.00 | 1.50 | 1.22 | 1.86 |
| | Intra-erythrocyte activity of ADI (U/mL) | 42.5 | 39.7 | 47.8 | 71.7 | 58.3 | 88.9 |
| | Extracellular activity (%) | 1.3 | 1.1 | 6.0 | 1.3 | 1.7 | 5.1 |
| | Intracellular activity (%) | 98.7 | 98.9 | 94.0 | 98.7 | 98.3 | 94.9 |

TABLE 7

Hematologic and biochemical characteristics of ERY-ADI I to VI (Day 7)

| | | ADI 3 mg/mL | | | ADI 5 mg/mL | | |
|---|---|---|---|---|---|---|---|
| | Day 7 parameters | ERY-ADI I | ERY-ADI II | ERY-ADI III | ERY-ADI IV | ERY-ADI V | ERY-ADI VI |
| Hemato-Logical data | Hematocrit (%) | 47.6 | 51.4 | 50.4 | 50.4 | 48.0 | 47.6 |
| | Corpuscular volume (fL) | 86.4 | 82.8 | 86.6 | 85.3 | 82.6 | 87.6 |
| | Corpuscular hemoglobin (g/dL) | 27.4 | 28.8 | 27.3 | 28.2 | 29.6 | 27.6 |
| | RBC count ($10^6$/μL) | 5.52 | 6.22 | 5.82 | 5.90 | 5.82 | 5.44 |
| | Total Hemoglobin (g/dL) | 13.0 | 14.8 | 13.8 | 14.2 | 14.2 | 13.2 |
| | Extracellular Hb (g/dL) | 0.3 | 0.5 | 0.5 | 0.4 | 0.5 | 0.5 |
| ADI | Intra-erythrocyte concentration of ADI (mg/mL of RBC) | 0.85 | 0.80 | 0.91 | 1.35 | 1.22 | 1.54 |
| | Intra-erythrocyte activity of ADI (U/mL) | 40.6 | 38.2 | 43.5 | 64.5 | 58.3 | 73.6 |
| | Extracellular activity (%) | 3.7 | 5.2 | 11.5 | 4.2 | 3.7 | 12.7 |
| | Intracellular activity (%) | 96.3 | 94.9 | 88.5 | 95.8 | 96.3 | 87.3 |

Entrapment of Arginine Deiminase in human red blood cells proved to be a very reproducible process. The main parameters were stable between Day 0 and Day 1 (e.g. extracellular hemoglobin, intracellular and extracellular enzyme activity, hematocrit, corpuscular volume). At Day 7, the measured parameters indicated that the ERY-ADI product is very stable in vitro, independently of the ADI concentration added before the entrapment process.

Conclusion. Arginine Deiminase (ADI; EC number 3.5.3.6) entrapped in red blood cells (RBC), was obtained using the Erytech's proprietary ERYCAPS® technology platform. The entrapment of therapeutic enzymes into red blood cells can provide effective, long-acting therapeutic activity with reduced toxicity.

Entrapment of Arginine Deiminase inside Red Blood Cells (ERY-ADI product), greatly improves the pharmacological properties of the enzyme. In healthy mice, plasma L-arginine depletion was complete within 15 minutes after administration and was sustained for 13 days.

When injected to Arginase-deficient mice, ERY-ADI demonstrated a spectacular efficacy on the very high blood L-arginine concentrations displayed by these mice. Indeed, 24 h after administration, blood L-arginine concentration was reduced by 52 and 92% when 4 or 8 mL/kg were injected, respectively. Three days after administration, blood L-arginine level remained reduced by 19 and 73%. Moreover, despite the production of ammonia by Arginine Deiminase, the serum level stayed comparable to the mock-loaded RBC control.

These results were confirmed in a second study wherein a single administration yielded a blood arginine depletion for at least 10 days and a second injection of ERY-ADI was well tolerated by arginase-deficient mice.

Entrapment of Arginine Deiminase was successfully performed in human Red Blood Cells with a good reproducibility and in vitro stability.

Based on these results, ERY-ADI is envisioned to be capable of counteracting the primary biochemical defect of the rare genetic disorder of Arginase deficiency.

The invention will now be described by the following numbered paragraphs:

1. A pharmaceutical composition comprising arginine deiminase (ADI) encapsulated into erythrocytes and optionally a pharmaceutically acceptable vehicle for its use in treating arginase-1 deficiency, preferably wherein the composition is capable of reducing pathological plasma or whole blood arginine levels in a patient or subject suffering from Arginase 1 (Arg1) deficiency to normal physiological or near-normal physiological plasma or whole blood arginine levels, more preferably wherein the composition is capable of reducing the pathological levels of arginine by at least about 20, 30, 40, 50, 60, 70 or about 80% for a period of at least about 6, 7, 8, 9, 10 or 11 days post administration of a single dose of the composition;

optionally wherein the ADI is any one, any combination, or all of the following: co-factor-independent, magnesium-independent, iron-independent, vitamin-independent, pro-vitamin-independent; and optionally wherein the composition is characterized by any or all of the following ranges of values across the indicated parameters:

Hematocrit (%): about 48 to about 51;

Corpuscular volume (fL): about 82 to about 88;

Corpuscular hemoglobin (g/dL): about 27 to about 30;

RBC count (106/μL): about 5.5 to about 6.2;

Total Hemoglobin (g/dL): about 13.0 to about 14.5;

Extracellular Hb (g/dL): about 0.1 to about 0.2;

Intra-erythrocyte concentration of ADI (mg/mL of RBC): about 0.8 to about 1.6;

Intra-erythrocyte activity of ADI (U/mL): about 42 to about 49 or about 65 to about 74;

Extracellular activity (%): about 0.0 to about 4.0;

Intracellular activity (%): about 96 to about 100; and/or

Entrapment yield of ADI (%): about 27 to about 34.

2. The pharmaceutical composition for the use according to paragraph 1, wherein said composition is a suspension having an osmolarity of between 270 and 350 mOsm/l.

3. The pharmaceutical composition for the use according to paragraph 1 or 2, wherein the pharmaceutically acceptable vehicle is a preservative solution comprising NaCl and Adenine.

4. The pharmaceutical composition for the use according to any one of paragraphs 1 to 3, wherein said ADI is from M. arginini.

5. The pharmaceutical composition for the use according to any one of paragraphs 1 to 4, wherein the ADI comprises the amino acid sequence of SEQ ID NO: 1 or a variant or fragment thereof.
6. The pharmaceutical composition for the use according to paragraphs 5, wherein said variant comprises an amino acid sequence that is at least 80% identical to the amino acid sequence SEQ ID NO: 1.
7. The pharmaceutical composition for the use according to paragraphs 5 or 6, wherein said variant or fragment retains the biological activity of the ADI having the amino acid sequence of SEQ ID NO: 1.
8. The pharmaceutical composition for the use according to any one of paragraphs 1 to 7, wherein the concentration of encapsulated ADI is from 0.1 to 7 mg/ml.
9. The pharmaceutical composition for the use according to any one of paragraphs 1 to 8, wherein the pharmaceutical composition is packaged in a dose having a volume from 10 to 250 ml.
10. The pharmaceutical composition for the use according to paragraph 9, wherein the amount of ADI encapsulated in one dose for a patient is from 0.01 mg/kg to 500 mg/kg of encapsulated ADI per kg body weight of said patient.
11. A suspension of erythrocytes encapsulating ADI from M. arginini.
12. The suspension of paragraph 11, wherein said ADI comprises the amino acid sequence of SEQ ID NO: 1 or a variant or fragment thereof.
13. The suspension of paragraph 12, wherein said variant comprises an amino acid sequence that is at least 80% identical to the amino acid sequence SEQ ID NO: 1.
14. A pharmaceutical composition comprising a suspension according to any one of paragraphs 11 to 13, for its use in treating arginase-1 deficiency or arginine-dependent cancers, treating or preventing of septic shock, inhibiting angiogenesis and treating angiogenesis associated diseases.
15. A method for treating arginase-1 deficiency or arginine-dependent cancers, treating or preventing of septic shock, inhibiting angiogenesis and treating angiogenesis associated diseases comprising administering to a patient or subject in need thereof the composition or suspension of any one of paragraphs 1 to 14.
16. A method for reducing pathological plasma arginine levels to normal physiological plasma arginine levels in a patient or subject chronically suffering from said pathological plasma arginine levels, comprising the step of administering more than one dose of the composition or suspension of any one of paragraphs 1 to 14.
17. The method of paragraph 16, wherein the pathological plasma arginine levels are in excess of about 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590 or 600 µM.
18. The method of paragraph 16 or 17, wherein the patient or subject has a known Arg1 mutation or exhibits less than about 5% arginase activity or substantially no arginase activity.
19. The method of paragraph 16 or 17, wherein the pathological plasma arginine levels are at least about 2, 3, 4, 5, 6, 7, 8, 9, 10, 11, 12, 13, 14, 15 or more fold higher than healthy subjects not suffering from pathological plasma arginine levels.
20. The method of any one of paragraphs 16 to 19, wherein one dose of the composition or suspension is sufficient to maintain non-pathological, normal physiological plasma arginine levels for at least about 1, 2, 3, 4, 5, 6, 7, 8, 9, 10, 11 or 12 weeks.
21. The method of any one of paragraphs 16 to 20, wherein the composition or suspension only needs to be administered once every 2 weeks or once every 4 weeks to maintain physiological plasma arginine levels.

The invention will now be described in the following non-limiting set of Claims.

---

The invention claimed is:

1. A method of treatment of arginase-1 deficiency, comprising administering to a patient in need thereof an effective amount of a pharmaceutical composition comprising a magnesium-independent arginine deiminase (ADI) encapsulated into erythrocytes and a pharmaceutically acceptable vehicle.

2. The method according to claim 1, wherein said composition is a suspension having an osmolarity of between 270 and 350 mOsm/L; and wherein the ADI further does not depend upon iron or manganese, or is co-factor-independent.

3. The method according to claim 1, wherein the pharmaceutically acceptable vehicle is a preservative solution comprising NaCl and Adenine.

4. The method according to claim 1, wherein the ADI is from *Mycoplasma arginini*.

5. The method according to claim 1, wherein the ADI comprises or consists essentially of the amino acid sequence of SEQ ID NO: 1.

6. The method according to claim 1, wherein the ADI comprises an amino acid sequence that is at least 80% identical to the amino acid sequence set forth in SEQ ID NO: 1.

7. The method according to claim 1, wherein the concentration of encapsulated ADI is from 0.1 to 7 mg/ml.

8. The method of claim 1, wherein the pharmaceutical composition is formulated as a dose having a volume from 10 to 250 ml.

9. The method of claim 8, wherein the dose comprises from 0.01 mg/kg to 500 mg/kg of encapsulated ADI per kg patient body weight.

10. A method of treatment of arginase-1 deficiency or arginine-dependent cancers, treating or preventing of septic shock, inhibiting angiogenesis and treating angiogenesis associated diseases, comprising administering to a patient in need thereof an effective amount of a suspension of erythrocytes encapsulating a magnesium-independent arginine deiminase from *Mycoplasma arginini*.

11. The method of claim 10, wherein said ADI comprises the amino acid sequence set forth in SEQ ID NO: 1.

12. The method of claim 10, wherein the ADI further neither requires iron nor manganese, and wherein a single administration of erythrocytes encapsulating the magnesium-independent ADI maintain depleted levels of arginine for more than 10 days.

13. The method of claim 12, wherein the ADI does not require any co-factor, and wherein a single administration of erythrocytes encapsulating the magnesium-independent ADI maintains depleted levels of arginine for more than 10 days.

14. The method of claim 1, further comprising reducing pathological plasma or whole blood arginine levels in a patient or subject suffering from Arginase 1 deficiency to normal physiological or near-normal physiological plasma or whole blood arginine levels, and wherein a single administration of erythrocytes encapsulating the magnesium-independent ADI maintain depleted levels of arginine for more than 10 days.

15. The method of claim 1, wherein the composition reduces pathological levels of arginine by at least about 50, 60, 70 or about 80% for a period of at least about 6, 7, 8, 9, 10 or 11 days post administration of a single dose of the composition; and wherein the ADI is also iron-independent and/or manganese-independent and/or co-factor independent.

16. The method of claim 1, wherein the composition is characterized by any or all of the following ranges of values across the indicated parameters: hematocrit (%): about 48 to about 51; corpuscular volume (fL): about 82 to about 88; corpuscular hemoglobin (g/dL): about 27 to about 30; RBC count ($10^6$/µl): about 5.5 to about 6.2; total hemoglobin (g/dL): about 13.0 to about 14.5; extracellular Hb (g/dL): about 0.1 to about 0.2; intra-erythrocyte concentration of ADI (mg/mL of RBC): about 0.8 to about 1.6; intra-erythrocyte activity of ADI (U/mL): about 42 to about 49 or about 65 to about 74; extracellular activity (%): about 0.0 to about 4.0; intracellular activity (%): about 96 to about 100; and/or entrapment yield of ADI (%): about 27 to about 34, and wherein a single administration of erythrocytes encapsulating the magnesium-independent ADI maintains depleted levels of arginine for more than 10 days.

17. The method of claim 2, further comprising reducing pathological plasma or whole blood arginine levels in a patient or subject suffering from Arginase 1 deficiency to normal physiological or near-normal physiological plasma or whole blood arginine levels, and wherein a single administration of erythrocytes encapsulating the magnesium-independent ADI maintains depleted levels of arginine for more than 10 days.

18. The method of claim 2, wherein the composition reduces pathological levels of arginine by at least about 50, 60, 70 or about 80% for a period of at least about 6, 7, 8, 9, 10 or 11 days post administration of a single dose of the composition; and wherein the ADI is also iron-independent and/or manganese-independent and/or co-factor independent.

19. The method of claim 2, wherein the composition is characterized by any or all of the following ranges of values across the indicated parameters: hematocrit (%): about 48 to about 51; corpuscular volume (fL): about 82 to about 88; corpuscular hemoglobin (g/dL): about 27 to about 30; RBC count ($10^6$/µL): about 5.5 to about 6.2; total hemoglobin (g/dL): about 13.0 to about 14.5; extracellular Hb (g/dL): about 0.1 to about 0.2; intra-erythrocyte concentration of ADI (mg/mL of RBC): about 0.8 to about 1.6; intra-erythrocyte activity of ADI (U/mL): about 42 to about 49 or about 65 to about 74; extracellular activity (%): about 0.0 to about 4.0; intracellular activity (%): about 96 to about 100; and/or entrapment yield of ADI (%): about 27 to about 34, and wherein a single administration of erythrocytes encapsulating the magnesium-independent ADI maintains depleted levels of arginine for more than 10 days.

\* \* \* \* \*

SEQUENCE LISTING

```
<160> NUMBER OF SEQ ID NOS: 1

<210> SEQ ID NO 1
<211> LENGTH: 410
<212> TYPE: PRT
<213> ORGANISM: Mycoplasma arginini

<400> SEQUENCE: 1

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110
```

-continued

```
Val Val Arg Asn Phe Leu Lys Ala Lys Lys Thr Ser Arg Glu Leu Val
        115                 120                 125
Glu Ile Met Met Ala Gly Ile Thr Lys Tyr Asp Leu Gly Ile Glu Ala
        130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Val Phe Ser
            180                 185                 190
Asn His Pro Lys Leu Ile Asn Thr Pro Trp Tyr Tyr Asp Pro Ser Leu
            195                 200                 205
Lys Leu Ser Ile Glu Gly Gly Asp Val Phe Ile Tyr Asn Asn Asp Thr
    210                 215                 220
Leu Val Val Gly Val Ser Glu Arg Thr Asp Leu Gln Thr Val Thr Leu
225                 230                 235                 240
Leu Ala Lys Asn Ile Val Ala Asn Lys Glu Cys Glu Phe Lys Arg Ile
                245                 250                 255
Val Ala Ile Asn Val Pro Lys Trp Thr Asn Leu Met His Leu Asp Thr
                260                 265                 270
Trp Leu Thr Met Leu Asp Lys Asp Lys Phe Leu Tyr Ser Pro Ile Ala
            275                 280                 285
Asn Asp Val Phe Lys Phe Trp Asp Tyr Asp Leu Val Asn Gly Gly Ala
            290                 295                 300
Glu Pro Gln Pro Val Glu Asn Gly Leu Pro Leu Glu Gly Leu Leu Gln
305                 310                 315                 320
Ser Ile Ile Asn Lys Lys Pro Val Leu Ile Pro Ile Ala Gly Glu Gly
                325                 330                 335
Ala Ser Gln Met Glu Ile Glu Arg Glu Thr His Phe Asp Gly Thr Asn
            340                 345                 350
Tyr Leu Ala Ile Arg Pro Gly Val Val Ile Gly Tyr Ser Arg Asn Glu
            355                 360                 365
Lys Thr Asn Ala Ala Leu Glu Ala Ala Gly Ile Lys Val Leu Pro Phe
    370                 375                 380
His Gly Asn Gln Leu Ser Leu Gly Met Gly Asn Ala Arg Cys Met Ser
385                 390                 395                 400
Met Pro Leu Ser Arg Lys Asp Val Lys Trp
                405                 410
```